United States Patent
Hosoda et al.

(10) Patent No.: US 10,453,238 B2
(45) Date of Patent: Oct. 22, 2019

(54) INFORMATION PROCESSING APPARATUS, INFORMATION PROCESSING METHOD, AND PROGRAM FOR DISPLAYING INFORMATION ON MULTIPLE DISPLAY LAYERS

(71) Applicant: SONY CORPORATION, Tokyo (JP)

(72) Inventors: Yasuhide Hosoda, Kanagawa (JP); Ryota Mihara, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/949,676

(22) Filed: Apr. 10, 2018

(65) Prior Publication Data
US 2018/0232926 A1    Aug. 16, 2018

Related U.S. Application Data

(63) Continuation of application No. 15/200,219, filed on Jul. 1, 2016, now Pat. No. 9,972,112, which is a
(Continued)

(30) Foreign Application Priority Data

May 30, 2013    (JP) ................ 2013-114006

(51) Int. Cl.
*H04N 13/346*    (2018.01)
*G06F 3/041*    (2006.01)
(Continued)

(52) U.S. Cl.
CPC ............. *G06T 11/60* (2013.01); *A61B 5/18* (2013.01); *G06F 3/041* (2013.01); *H04N 13/346* (2018.05);
(Continued)

(58) Field of Classification Search
CPC .... G06T 11/60; H04N 13/395; H04N 13/346; H04N 13/398; G06F 3/0416; G06F 3/041;
(Continued)

(56) References Cited

U.S. PATENT DOCUMENTS 6,927,694 B1 * 8/2005 Smith ................ B60K 28/066
                                                  340/573.1
7,205,959 B2    4/2007 Henriksson
(Continued)

FOREIGN PATENT DOCUMENTS

JP    2004-356731    12/2004
JP    2005-312686    11/2005
(Continued)

OTHER PUBLICATIONS

Japanese Office Action dated May 16, 2017 for Japanese Application No. 2013-114006, 4 pages.
(Continued)

*Primary Examiner* — Jonathan A Boyd
(74) *Attorney, Agent, or Firm* — Xsensus LLP

(57) ABSTRACT

There is provided an information processing apparatus, including a display control section which determines which display layers out of a plurality of mutually overlapping display layers information is to be displayed on based on parameters associated with the information.

19 Claims, 41 Drawing Sheets

Related U.S. Application Data continuation of application No. 14/283,398, filed on May 21, 2014, now Pat. No. 9,715,752.

(51) Int. Cl.

| | | |
|---|---|---|
| *G06T 11/60* | (2006.01) | |
| *H04N 13/398* | (2018.01) | |
| *A61B 5/18* | (2006.01) | |
| *H04N 13/395* | (2018.01) | |
| *A61B 5/021* | (2006.01) | |
| *A61B 5/024* | (2006.01) | |
| *A61B 5/00* | (2006.01) | |

(52) U.S. Cl.
CPC ........ *H04N 13/395* (2018.05); *H04N 13/398* (2018.05); *A61B 5/021* (2013.01); *A61B 5/024* (2013.01); *A61B 5/4866* (2013.01); *A61B 5/4872* (2013.01)

(58) Field of Classification Search
CPC ........... A61B 5/18; A61B 5/021; A61B 5/024; A61B 5/4866; A61B 5/4872
See application file for complete search history.

(56) References Cited

U.S. PATENT DOCUMENTS

| | | | | |
|---|---|---|---|---|
| 7,724,208 | B1* | 5/2010 | Engel | G02B 27/2278 345/4 |
| 2007/0252804 | A1 | 11/2007 | Engel | |
| 2011/0105925 | A1 | 5/2011 | Hatakeyama | |
| 2011/0228980 | A1 | 9/2011 | Ichikawa | |
| 2011/0249026 | A1 | 10/2011 | Singh | |
| 2012/0060089 | A1 | 3/2012 | Heo | |
| 2012/0212353 | A1* | 8/2012 | Fung | B60K 28/06 340/905 |
| 2012/0218295 | A1* | 8/2012 | Hashikawa | B60K 35/00 345/629 |
| 2013/0083040 | A1 | 4/2013 | Prociw | |
| 2013/0300728 | A1 | 11/2013 | Reichow | |
| 2014/0168243 | A1* | 6/2014 | Huang | G06T 1/20 345/522 |

FOREIGN PATENT DOCUMENTS

| | | |
|---|---|---|
| JP | 2007-105097 | 4/2007 |
| JP | 2007-514181 | 5/2007 |
| JP | 2007-171154 | 7/2007 |
| JP | 2008-302741 | 12/2008 |
| JP | 2009-053539 | 3/2009 |
| JP | 2009-075988 | 4/2009 |
| JP | 2011-038346 | 2/2011 |
| JP | 2013-011645 | 1/2013 |
| JP | 2014-232484 | 12/2014 |

OTHER PUBLICATIONS

Office Action dated Jan. 17, 2018 in corresponding Chinese Application No. 201410219932.5 (with English translation).

Japanese Office Action dated Jul. 3, 2018 in Japanese Application No. 2017-153107.

Combined Chinese Office Action and Search Report dated Jan. 17, 2018 in Patent Application No. 201410219932.5 (with English language translation).

* cited by examiner

INFORMATION PROCESSING APPARATUS, INFORMATION PROCESSING METHOD, AND PROGRAM FOR DISPLAYING INFORMATION ON MULTIPLE DISPLAY LAYERS

CROSS REFERENCE TO RELATED APPLICATIONS

The present application is a continuation application of U.S. patent application Ser. No. 15/200,219, filed Jul. 1, 2016, which is a continuation of U.S. patent application Ser. No. 14/283,398, filed May 21, 2014, now U.S. Pat. No. 9,715,752, which claims the priority from prior Japanese Priority Patent Application JP 2013-114006 filed in the Japan Patent Office on May 30, 2013, the entire contents of each of which is hereby incorporated by reference.

BACKGROUND

The present disclosure relates to an information processing apparatus, an information processing method and a program.

An information processing apparatus disclosed in JP 2009-53539A has a plurality of mutually overlapping display layers, and displays information on each of the display layers.

SUMMARY

However, JP 2009-53539A is limited to disclosing an information processing apparatus such as described above, and there is no disclose for determining how information is to be displayed on each of the display layers. Therefore, it is not able to be said that the display layers are effectively used. Accordingly, technology has been sought after which is able to more effectively use each of the display layers.

According to an embodiment of the present disclosure, there is provided an information processing apparatus, including a display control section which determines which display layers out of a plurality of mutually overlapping display layers information is to be displayed on based on parameters associated with the information.

According to an embodiment of the present disclosure, there is provided an information processing method, including determining which display layers out of a plurality of mutually overlapping display layers information is to be displayed on based on parameters associated with the information.

According to an embodiment of the present disclosure, there is provided a program for causing a computer to function as a display control function which determines which display layers out of a plurality of mutually overlapping display layers information is to be displayed on based on parameters associated with the information.

According to the present disclosure such as described above, since information displayed on each of the display layers is determined based on parameters associated with this information, the display layers can be more effectively used.

DETAILED DESCRIPTION OF THE EMBODIMENT(S)

Figure 1A:
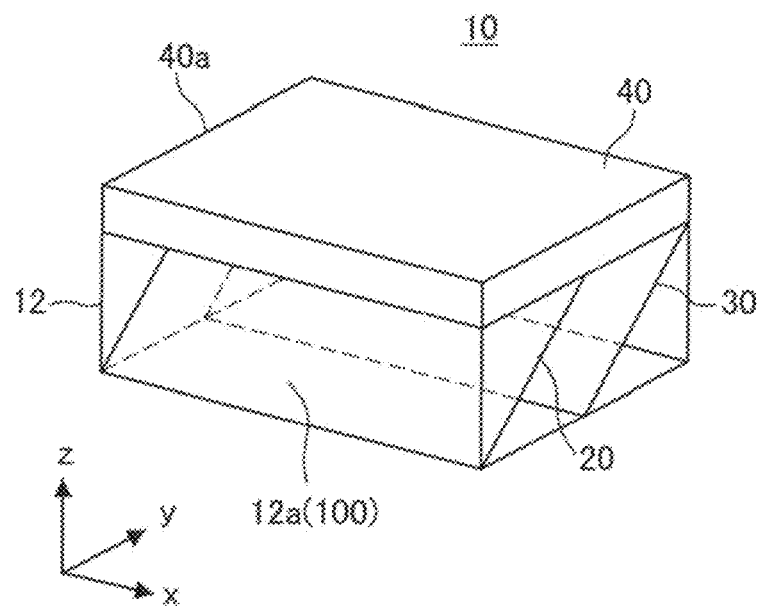
FIG. 1A is a perspective view which shows an external appearance configuration of an information processing apparatus according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.
1. External appearance configuration of the information processing apparatus
2. Internal configuration of the information processing apparatus
3. Basic operations of the information processing apparatus
4. Various display examples

1. EXTERNAL APPEARANCE CONFIGURATION OF THE INFORMATION PROCESSING APPARATUS

First, an external appearance configuration of an information processing apparatus 10 according to an embodiment of the present disclosure will be described in detail based on FIG. 1. FIG. 1A is a perspective view which shows an external appearance configuration of the information processing apparatus 10, and FIG. 1B is a cross-sectional view which shows an external appearance configuration of the information processing apparatus 10.

Figure 1B:
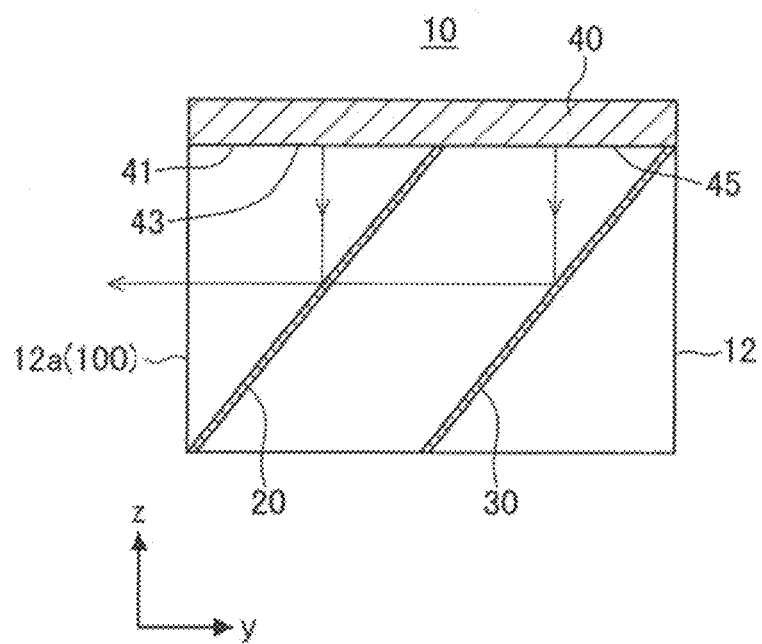
FIG. 1B is a cross-sectional view which shows an external appearance configuration of the information processing apparatus according to the same embodiment.

As shown in FIG. 1A and FIG. 1B, the information processing apparatus 10 according to the present embodiment includes a half mirror 20, a mirror 30, a display section 40 and a touch panel 100 as this external appearance configuration.

The half mirror 20 is included within a housing 12 of the information processing apparatus 10. Here, the surface through which light reflected from the half mirror 20 and the mirror 30 passes (hereinafter, called a "front surface 12a"), from among the side surfaces of the housing 12, is constituted by a transparent member. The front surface of the information processing apparatus 10 is a surface opposite to the viewpoint of a user. As shown in FIG. 1B, the half mirror 20 is inclined towards an interior direction of the information processing apparatus 10 (that is, a y-axis positive direction). The mirror 30, which is inclined similar to that of the half mirror 20, is arranged on a further interior side of this half mirror 20, that is, on the y-axis positive direction side. The half mirror 20 and the mirror 30 overlap in the y-axis direction.

The half mirror 20 is a mirror through which incident light passes from a rear side of this half mirror (that is, the y-axis positive direction side), and which reflects incident light from the front side of the half mirror. Further, the mirror 30 is a mirror through which incident light does not pass from a rear side of this mirror (the y-axis positive direction side), and which reflects incident light from the front side of the mirror.

The display section 40 capable of displaying information such as text (character) information or image information is arranged above the half mirror 20 and the mirror 30 (that is, in a z-axis positive direction). The display section 40 is built into a housing 40a. As shown in FIG. 1B, the display section 40 is arranged so that a display screen 41 faces the half mirror 20 and mirror 30 side (that is, a z-axis negative direction side). By having the display section 40 set arranged such as this, the display screen 41 is divided into two display regions by the upper sides of the half mirror 20 and the mirror 30.

Further, information displayed on the display screen positioned above the half mirror 20 (hereinafter, called a first display region 43) is reflected by the half mirror 20, and is directed towards the front surface 12a of the information processing apparatus 10. Information displayed on the display screen positioned above the mirror 30 (hereinafter, called a second display region 45) is reflected by the mirror 30, and is directed towards the front surface 12a of the information processing apparatus 10 by passing through the half mirror 20.

Therefore, a user recognizes that respective information is displayed as if on the half mirror 20 and the mirror 30, and that this information overlaps at the front surface 12a of the information processing apparatus 10. That is, the user recognizes information displayed on the mirror 30 as if it is displayed on the interior side of the information processing apparatus 10, and recognizes information displayed on the half mirror 20 as if it is displayed on the near side of the information processing apparatus 10. Therefore, the half mirror 20 and the mirror 30 constitute separate display layers. The mirror 30 is arranged at a position (interior side) farther from the viewpoint of the user than that of the half mirror 20. Hereinafter, the half mirror 20 will be called a "near side display layer", and the mirror 30 will be called an "interior side display layer".

Note that, the user can select whether information of the interior side display layer is recognized or whether information of the near side display layer is recognized, by adjusting the focal point of the eyes. Further, by adjusting the focal point for which display layer will be displayed, since the display of the other display layer will be seen to be blurred, it will be difficult for an uncomfortable feeling to occur, even if plural amounts of information are displayed which mutually overlap.

By the above described configuration, the information processing apparatus 10 is capable of performing display of information which has depth, and can perform stereographic display of information. Here, for example, it is possible for a display device, such as a CRT display device, a liquid crystal display device, a plasma display device, an EL display device or a lamp, to be used as the display section 40 according to the present embodiment. The touch panel 100 is included on the front surface 12a of the housing 12.

While a description has been made in the above described description in the case where the display screen of the display section 40 is divided into two display regions by using one half mirror 20, the display screen of the display section 40 may be divided into N+1 display regions by using N half mirrors. By increasing the number of half mirrors to be used, it becomes possible for the display of information to be more hierarchized, and more information can be displayed without changing the size of the display section 40. That is, in this case, the number of display layers can become N+1. Further, the half mirror 20 may be capable of being moved in the y-axis direction. In this case, the size of the first display region 43 and the second display region 45 changes in accordance with the position of the half mirror 20.

Note that, while a description has been made in the above described embodiment in the case where the upper sides of the half mirror 20 and the mirror 30 are inclined towards the interior direction of the housing, and the display section 40 is arranged above the half mirror 20 and the mirror 30, the lower sides of the half mirror 20 and the mirror 30 may be inclined towards the interior direction of the housing, and the display section 40 may be arranged below the half mirror 20 and the mirror 30.

2. INTERNAL CONFIGURATION OF THE INFORMATION PROCESSING APPARATUS

Figure 2:
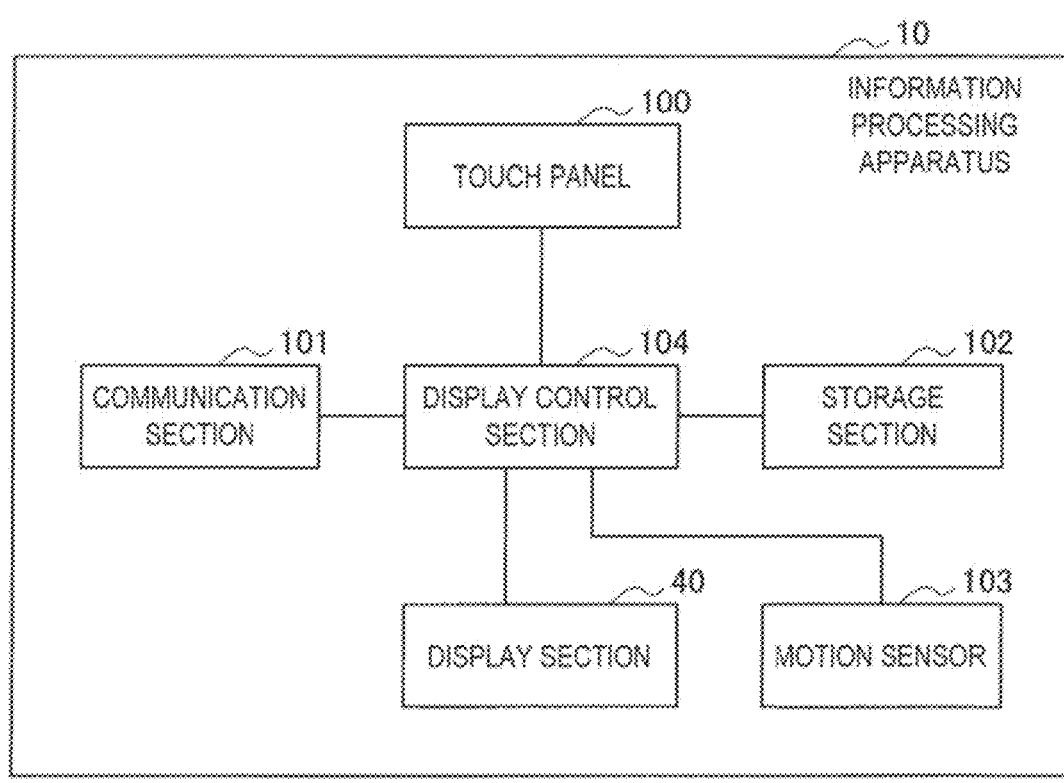
FIG. 2 is a block diagram which shows an internal configuration of the information processing apparatus.

Next, an internal configuration of the information processing apparatus 10 will be described based on FIG. 2. The information processing apparatus 10 includes a touch panel 100, a communication section 101, a storage section 102, a motion sensor 103, a display control section 104, and a display section 40. The information processing apparatus 10 includes hardware configurations such as a CPU, a ROM, a RAM, a communication apparatus, a display, a touch panel and a motion sensor. Programs for implementing the communication section 101, the storage section 102 and the display control section 104 in the information processing apparatus are recorded in at least the ROM. The CPU reads and executes the programs recorded in the ROM. Therefore, the touch panel 100, the communication section 101, the storage section 102, the motion sensor 103, the display control section 104 and the display section 40 are implemented by these hardware configurations. For example, the CPU, the ROM, the RAM, the communication apparatus, the display and the motion sensor are built into the housing 40a.

The touch panel 100 is included on the front surface 12a of the information processing apparatus 10 such as described above, and is press operated by a user. The touch panel 100 outputs operation information corresponding to a pressed position to the display control section 104. The communication section 101 acquires various types of information by communicating with various types of communication equipment. Here, other than information to be shown on the display section 40, information which shows a present position of a vehicle or the like, in the case where the information processing apparatus 10 is an on-board device of a car navigation system, can also be included as information acquired by the communication section 101. The communication section 101 outputs the acquired information to the display control section 104.

Other than the above described programs, the storage section 102 also stores information to be displayed on the display section 40 (hereinafter, called "display target information"). Here, for example, the display target information is not particularly limited, and is text information or image information. Further, the storage section 102 stores the information to be displayed on the display section 40 and the priorities (parameters) of this information in association with each other. Here, the priority is a parameter for determining which of the near side display layer and the interior side display layer information is to be displayed on. It becomes easier for the display target information having this priority to be displayed on the near side display layer as the priority increases. The priority of the display target information tends to increase in the case where it is estimated that this display target information is necessary for the user. It is needless to say that the parameters associated with the display target information are not limited to that of the priority. That is, the parameters associated with the display target information may be parameters for determining which of the near side display layer and the interior side display layer the display target information is to be displayed on.

The motion sensor 103 detects operations of the user (movements of the hands, head, line of sight or the like), and outputs this result to the display control section 104. For example, other than performing control of the entire information processing apparatus 10, the display control section 104 also performs the following processes. That is, the display control section 104 determines the display target information to be displayed on the near side display layer and the interior side display layer, based on the priorities associated with this display target information. That is, the display control section 104 determines which display layer display target information is to be displayed on, based on the priority associated with this display target information. For example, the display control section 104 may compare the priorities associated with two types of display target information, may display the display target information with the highest priority on the near side display layer, and may display the display target information with the lowest priority on the interior side display layer. Further, the display control section 104 may set a threshold in advance, may display the display target information with a priority higher than the threshold on the near side display layer, and may display the display target information with a priority lower than the threshold on the interior side display layer. Further, the display control section 104 may adjust the priority of each type of display target information, based on input operations of the touch panel 100, operations of the user or the like.

3. BASIC OPERATIONS OF THE INFORMATION PROCESSING APPARATUS

Figure 3:
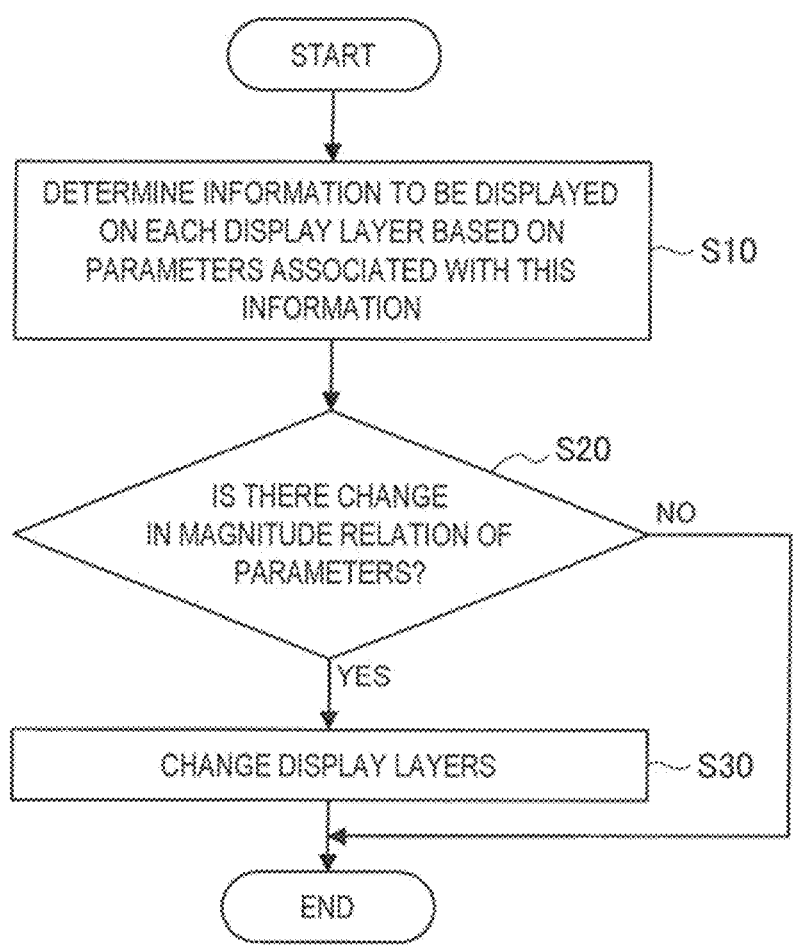
FIG. 3 is a flow chart which shows basic operations by the information processing apparatus.

Next, basic operations of the information processing apparatus 10 will be described based on the flow chart shown in FIG. 3. In step S10, the display control section 104 determines display target information to be displayed on each of the display layers, based on parameters, that is, priorities, associated with the display target information. Then, the display control section 104 displays this determined display target information on each of the display layers. For example, the display control section 104 compares the priorities associated with two types of display target information, displays the display target information with the highest priority on the near side display layer, and displays the display target information with the lowest priority on the interior side display layer. Here, the display control section 104 may reduce the visibility of the interior side display layer more than the visibility of the near side display layer. In this way, the user can more easily and visually recognize the display target information displayed on the near side display layer. For example, a method which reduces luminance, or a method which shades off colors by a filter adjusting the lighting and shading of colors, can be included as a method which reduces visibility.

In step S20, the display control section 104 adjusts the priorities of the display target information displayed on each of the display layers, based on input operations of the touch panel 100, operations of the user or the like. Then, the display control section 104 determines whether or not there has been a change in the magnitude relation of the priorities, specifically, whether or not the priority of the display target information displayed on the near side display layer has become smaller than the priority of the display target information displayed on the interior side display layer. In the case where it is determined that there has been a change in the magnitude relation of the priorities, the display control section 104 proceeds to step S30, and in the case where it is determined that there has been no change in the magnitude relation of the priorities, the display control section 104 ends the present process.

In step S30, the display control section 104 switches the display target information displayed on the near side display layer and the display target information displayed on the interior side display layer. That is, the display control section 104 moves the display target information displayed on the near side display layer to the interior side display layer, and moves the display target information displayed on the interior side display layer to the near side display layer. Afterwards, the display control section 104 ends the present process.

4. VARIOUS DISPLAY EXAMPLES

Next, various display examples by the information processing apparatus 10 will be described. While a description will be made as an example in the following description in the case where the information processing apparatus 10 is an on-board device of a car navigation system, it is needless to say that it is possible for the information processing apparatus 10 to be applied to an apparatus other than this. For example, the information processing apparatus 10 may be applied to a display device for the home. In the case where the information processing apparatus 10 is an on-board device of a car navigation system, for example, the information processing apparatus 10 is embedded within the dashboard of a vehicle. Also, the front surface 12a of the information processing apparatus 10 is directed towards the user side (for example, the driver side). For example, since the user is a driver, in the case where the information processing apparatus 10 is an on-board device of car navigation, the user will not be able to gaze at the information processing apparatus 10, in particular, while driving. Therefore, it is preferable that the information processing apparatus 10 is implemented so that the user is able to more intuitively and easily understand the display target information.

(Movement Between Display Layers in Accordance with a Luminance Exchange)

As described above, in the case where the magnitude relation of priorities has changed, the display control section 104 moves the display target information between display layers. For example, the display control section 104 may erase the display target information displayed by one of the display layers, and then may move the display target information by displaying the display target information on the other display layer. However, if the display target information is moved between display layers in accordance with a luminance exchange, it becomes possible to be implemented with more impact.

Figure 4:
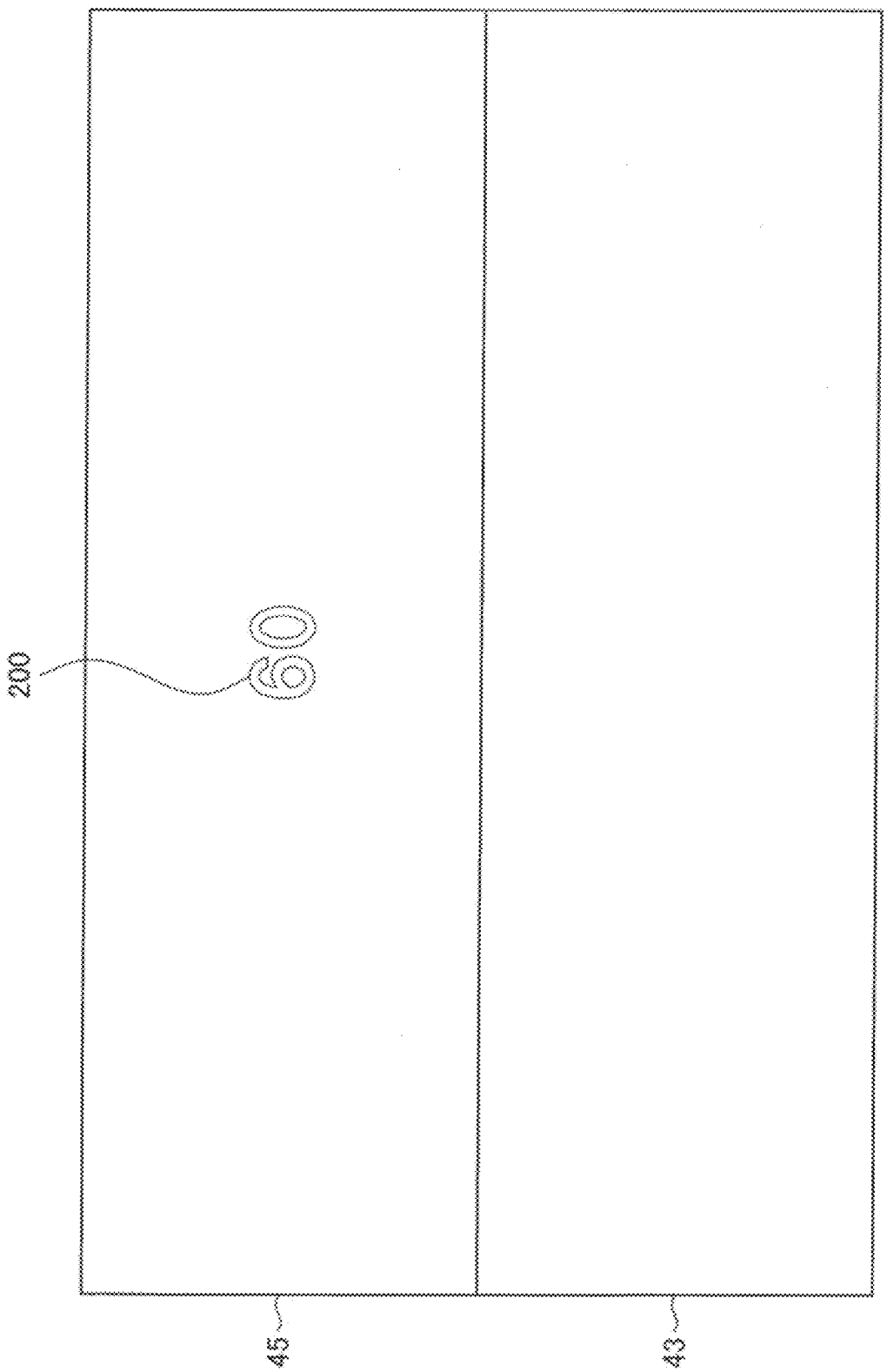
FIG. 4 is an explanatory diagram which shows an example of an image displayed on a display section.
Figure 5:
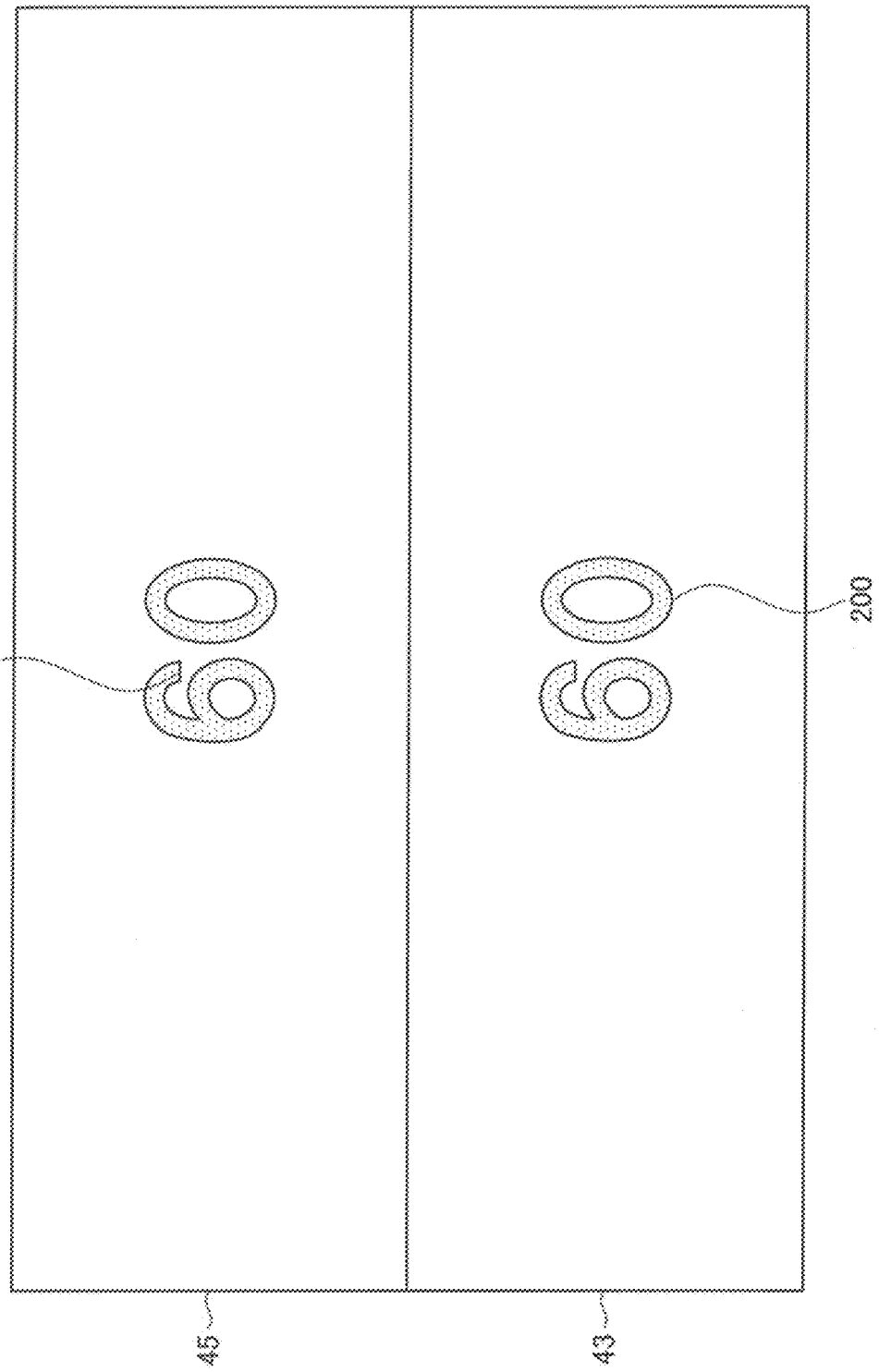
FIG. 5 is an explanatory diagram which shows an example of an image displayed on a display section.
Figure 6:
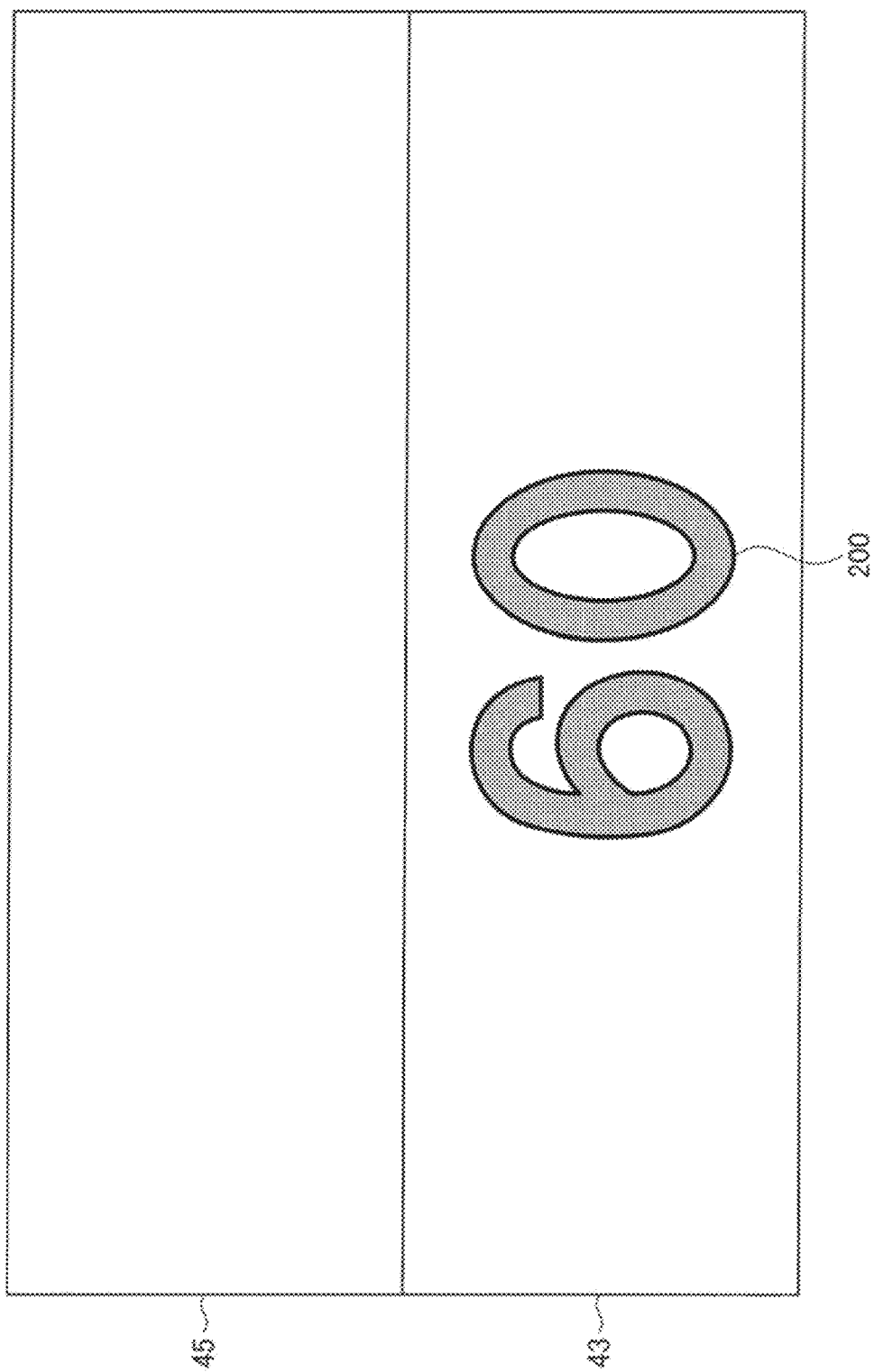
FIG. 6 is an explanatory diagram which shows an example of an image displayed on a display section.

Movement between display layers in accordance with a luminance exchange will be described based on FIG. 4 to FIG. 6. FIG. 4 to FIG. 6 show display target information displayed on the first display region 43 and the second display region 45 of the display section 40. FIG. 4 to FIG. 6 implement luminance by performing lighting and shading of a hatching. The luminance increases as the hatching becomes thicker. The display target information displayed on the first display region 43 is displayed on the near side display layer, and the display target information displayed on the second display region 45 is displayed on the interior side display layer. Here, an example will be described in which vehicle speed information (information of a speed meter) 200 moves from the interior side display layer to the near side display layer while being enhanced, and an integrated value of luminance (an integrated value of the luminance of the near side display layer and the luminance of the interior side display layer) increases. Note that, the luminance visually recognized by the user is an integrated value of the luminance of the near side display layer and the luminance of the interior side display layer.

As shown in FIG. 4, first, the display control section 104 displays vehicle speed information 200 on the interior side display layer with a low luminance. Next, the display control section 104 enhances the luminance of the vehicle speed information 200 while being raised within the interior side display layer.

In the case where the vehicle speed information 200 becomes some prescribed size, the display control section 104 displays the vehicle speed information 200 at a position within the near side display layer, which overlaps the vehicle speed information 200 within the interior side display layer, such as shown in FIG. 5. Here, the luminance of the vehicle speed information 200 displayed on each of the display layers becomes half the luminance of the vehicle speed information 200 displayed on the interior side display layer immediately before. By performing such an adjustment, the integrated value of luminance can be continuously changed.

Afterwards, the display control section 104 enlarges the vehicle speed information 200 displayed on each of the display layers (changes the size of the vehicle speed information 200 in a same state). On the other hand, the display control section 104 reduces the luminance of the vehicle speed information 200 within the interior side display layer (reduces the visibility), and raises the luminance of the vehicle speed information 200 within the near side display layer (raises the visibility). That is, the display control section 104 performs a luminance exchange. Here, a method which reduces the luminance of each of the pixel themselves, a method which reduces the luminance of a portion of pixels to zero or an extremely low value (that is, thins out the pixels) or the like, can be included as a method which reduces the luminance.

Afterwards, as shown in FIG. 6, the display control section 104 erases the vehicle speed information 200 from the interior side display layer, and displays the vehicle speed information 200 on the near side display layer. By the above described series of processes, the user can intuitively know the vehicle speed information 200 in the direction the user himself or herself is approaching. Here, the display control section 104 may perform this process during acceleration (when the value of the vehicle speed information 200 rises). In this case, the user can more intuitively understand that the vehicle is accelerating.

While the display control section 104 increases the integrated value of luminance in the above described example, the display control section 104 may perform the above described processes while the integrated value of the luminance is made constant. Further, the display control section 104 may perform the above described processes while the size of the vehicle speed information 200 is made constant. Further, the display control section 104 may perform the above described processes while the integrated value of the luminance and the size of the vehicle speed information 200 are made constant. Further, the display control section 104 may perform the above described processes while changing the color of the vehicle speed information 200. For example, the display control section 104 may perform the above described processes while increasing the color saturation of the vehicle speed information 200.

By performing the above described processes in reverse, the display control section 104 can move the vehicle speed information 200 from the interior side display layer to the near side display layer while being reduced, and can reduce the integrated value of the luminance (the luminance visually recognized by the user). The display control section 104 may perform such processes during deceleration of the vehicle, for example.

(Three-Dimensional Display)

Next, a three-dimensional display will be described. As described above, since display target information is displayed on both the interior side display layer and the near side display layer, the display control section 104 can stereographically display (three-dimensionally display) this display target information. However, the display control section 104 can further increase the stereoscopic effect by devising a display method of the display target information.

Figure 7:
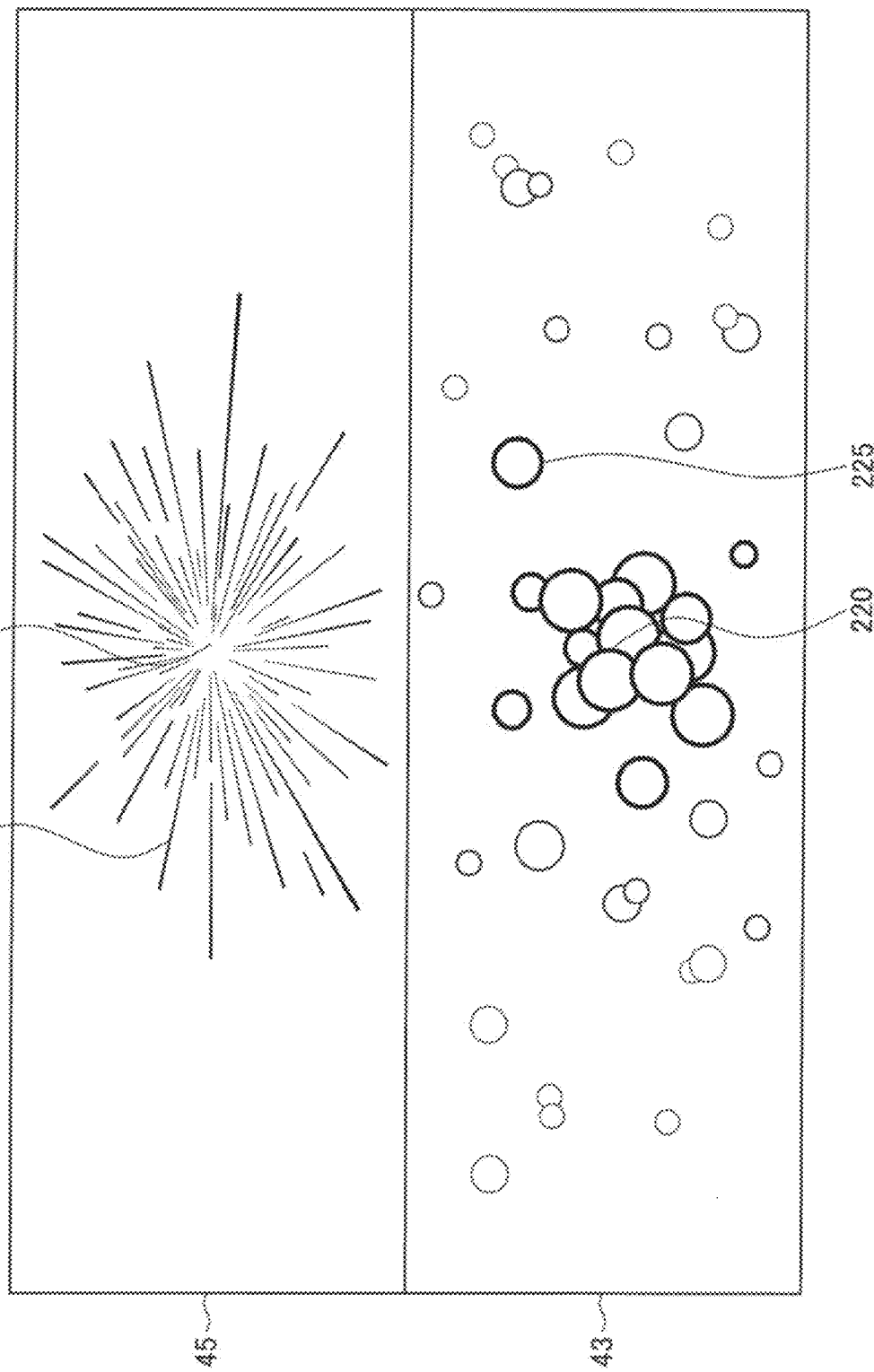
FIG. 7 is an explanatory diagram which shows an example of an image displayed on a display section.
Figure 8:
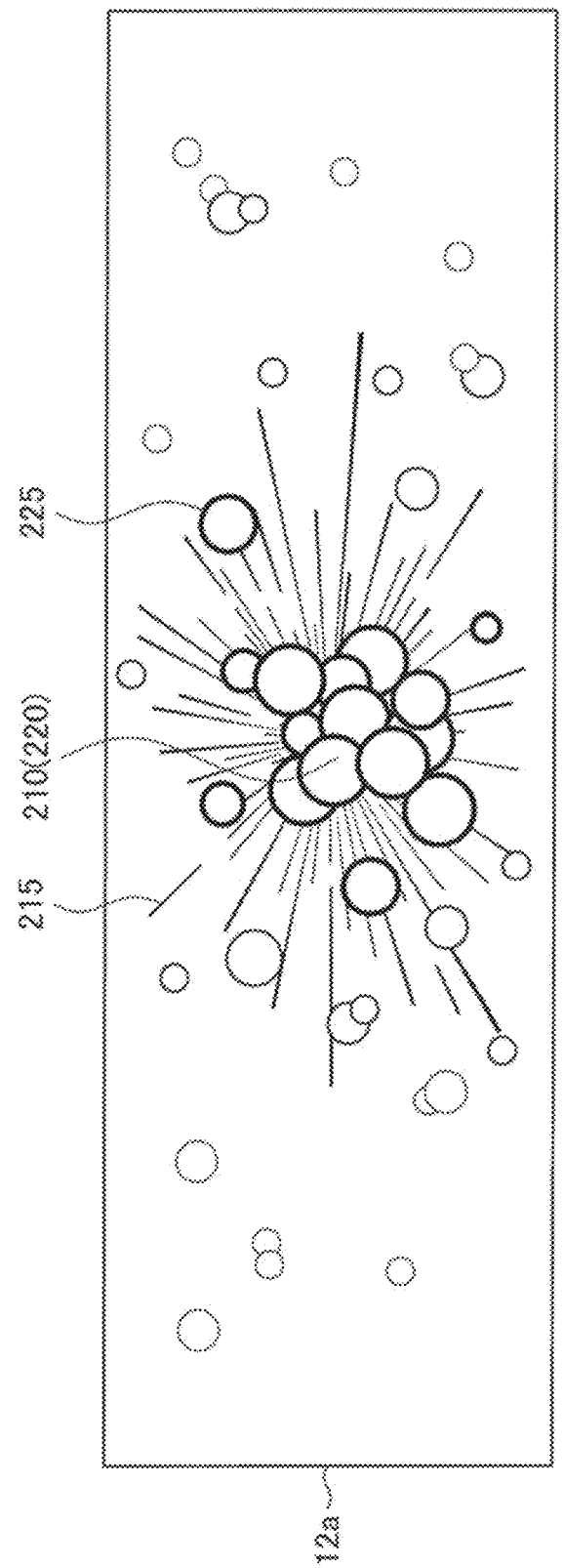
FIG. 8 is an explanatory diagram which shows an example of an image displayed on the front surface of the information processing apparatus.

Here, a three-dimensional display will be described based on FIG. 7 and FIG. 8. FIG. 7 shows display target information displayed on the first display region 43 and the second display region 45 of the display section 40. FIG. 8 shows display target information displayed on the front surface 12a of the information processing apparatus 10 (that is, display target information displayed on one of the display layers which is overlapping display target information displayed on the other display layer).

In this example, the display control section 104 sets reference points 210 and 220 at the central portions of the interior side display layer and the near side display layer. Also, the display control section 104 moves line images 215 from the outer edges of the interior side display layer towards the reference point 210, and terminates the line images at the reference point 210. In addition, the display control section 104 moves bubble images 225 from the outer edges of the near side display layer towards the reference point 220. Therefore, the user can intuitively know that the bubble images 225 move towards the interior side as if within a three-dimensional space. Note that, the display control section 104 may display the bubble images 225 on the interior side display layer and the line images 215 on the near side display layer.

(Navigation)

Next, navigation performed by the information processing apparatus 10 will be described. An on-board device of car navigation often displays map information. The information processing apparatus 10 can also display map information. However, since the information processing apparatus 10 has a plurality of display layers, information other than map information can be displayed overlapping the map information. That is, since the information processing apparatus 10 can provide the user with a greater variety of information, more appropriate navigation can be performed. That is, the information processing apparatus 10 according to the present embodiment is anticipated to be used as next-generation car navigation.

Figure 9:
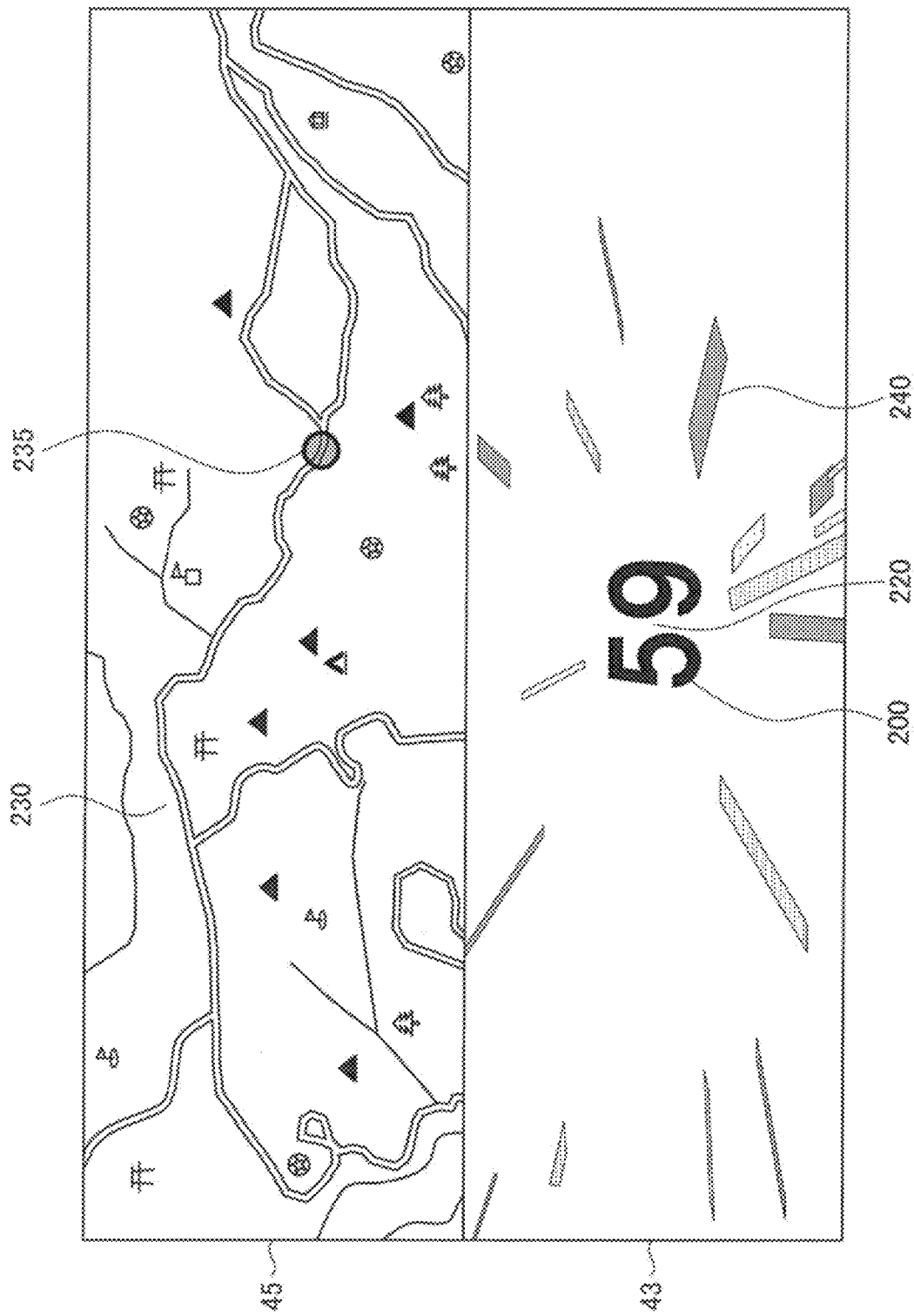
FIG. 9 is an explanatory diagram which shows an example of an image displayed on the display section.
Figure 10:
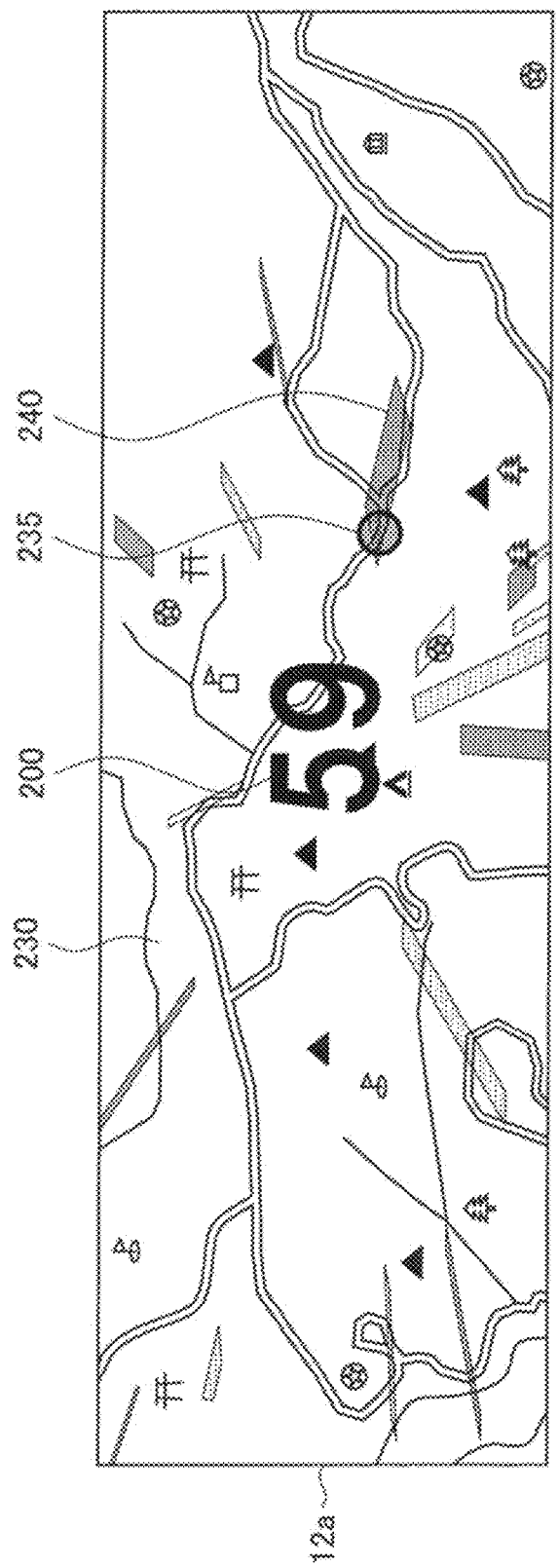
FIG. 10 is an explanatory diagram which shows an example of an image displayed on the front surface of the information processing apparatus.

An example of navigation performed by the information processing apparatus 10 is shown in FIG. 9 and FIG. 10. FIG. 9 shows display target information displayed on the first display region 43 and the second display region 45 of the display section 40. FIG. 10 shows display target information displayed on the front surface 12a of the information processing apparatus 10.

The display control section 104 displays map information 230 and a present position marker 235 on the interior side display layer, and displays vehicle speed information 200 and rectangular images 240 on the near side display layer. Here, the vehicle speed information 200 is an example of vehicle travelling information related to travelling of the vehicle. The display control section 104 sets a reference point 220 at the central portion of the near side display layer, and moves the rectangular images 240 from the reference point of the near side display layer towards to outer edges. Therefore, the user can intuitively know that the map information 230 and the vehicle speed information 200 are displayed within a three-dimensional space. Further, since the user can intuitively know that the rectangular images 240 are moving towards the near side, the user can intuitively know that the vehicle of the user is travelling. Further, the visibility of the map information 230 may be reduced so that the vehicle speed information 200 stands out. For example, the display control section 104 may reduce the luminance of the map information 230, or may shade the map information 230 by a filter which adjusts the lighting and shading of the colors. Further, the vehicle speed information 200 may be displayed with colors different to those of the map information 230 so that the vehicle speed information 200 stands out. In this way, the user can more intuitively understand the vehicle speed. The rectangular images 240 may be displayed by each of the examples shown below.

Here, in the example shown in FIG. 9, the priority of the vehicle speed information 200 is higher than the priority of the map information 230. However, in the case where the user gazes at the information processing apparatus 10 (it is possible for such gazing to be detected by the motion sensor 103), there is the possibility that the map information 230 will be more necessary for the user than the vehicle speed information 200. Accordingly, in the case where the user gazes at the information processing apparatus 10, the display control section 104 may reduce the priority of the vehicle speed information 200 more than the priority of the map information 230, and may switch the display layers of this information. Further, in the case where the user makes another gesture operation, for example, a gesture of swiping a hand in front of the information processing apparatus 10, the display control section 104 may reduce the priority of the vehicle speed information 200 more than the priority of the map information 230. Further, in the case where some audio guidance is performed (audio guidance such as asking to turn right at the next intersection), the display control section 104 may display the map information 230 on the near side display layer, and may display the vehicle speed information 200 on the interior side display layer. Further, in the case where the map information 230 is moved to the near side display layer, the display control section 104 may continue to display the vehicle speed information 200 on the near side display layer. In this case, the display control section 104 may display the vehicle speed information 200 and the map information 230 in a state capable of being differentiated (for example, differences, luminance, colors or the like).

Further, the display control section 104 may perform a movement process between display layers in accordance with the above described luminance exchange, when the vehicle speed information 200 and map information 230, in particular, the vehicle speed information 200, is moved between display layers. Further, the display control section 104 may enlarge the vehicle speed information 200 within the same layer during acceleration, and may emphasize the luminance and colors. Similarly, the display control section 104 may reduce the vehicle speed information 200 within the same layer during deceleration, and may attenuate the luminance and colors.

Further, the display control section 104 may display not only the vehicle speed information 200, but also tachometer information, remaining fuel amount information, water temperature information, distance meter information or the like, along with the vehicle speed information 200 or instead of the vehicle speed information 200, as vehicle travelling information.

Figure 11:
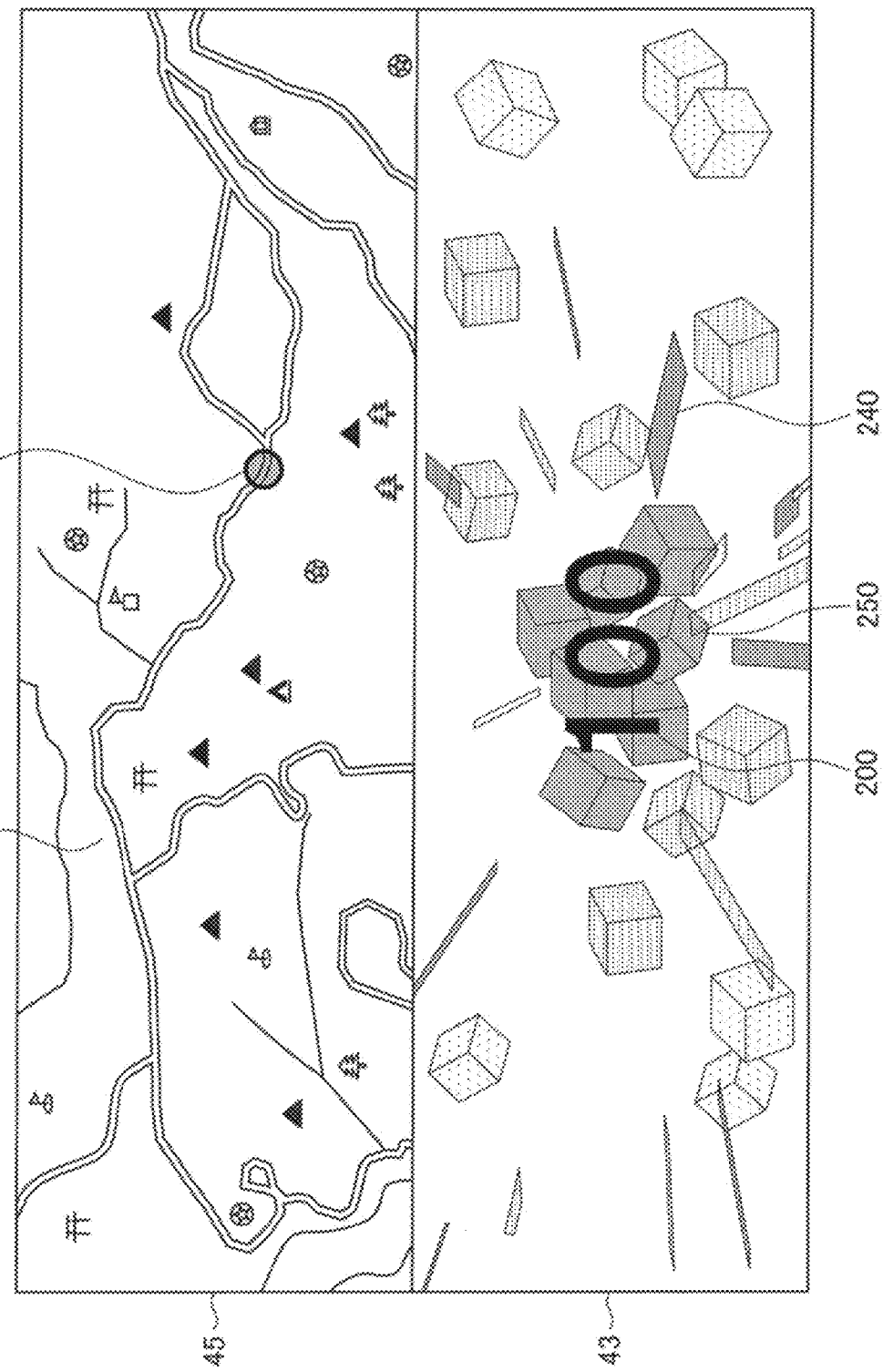
FIG. 11 is an explanatory diagram which shows an example of an image displayed on the display section.
Figure 12:
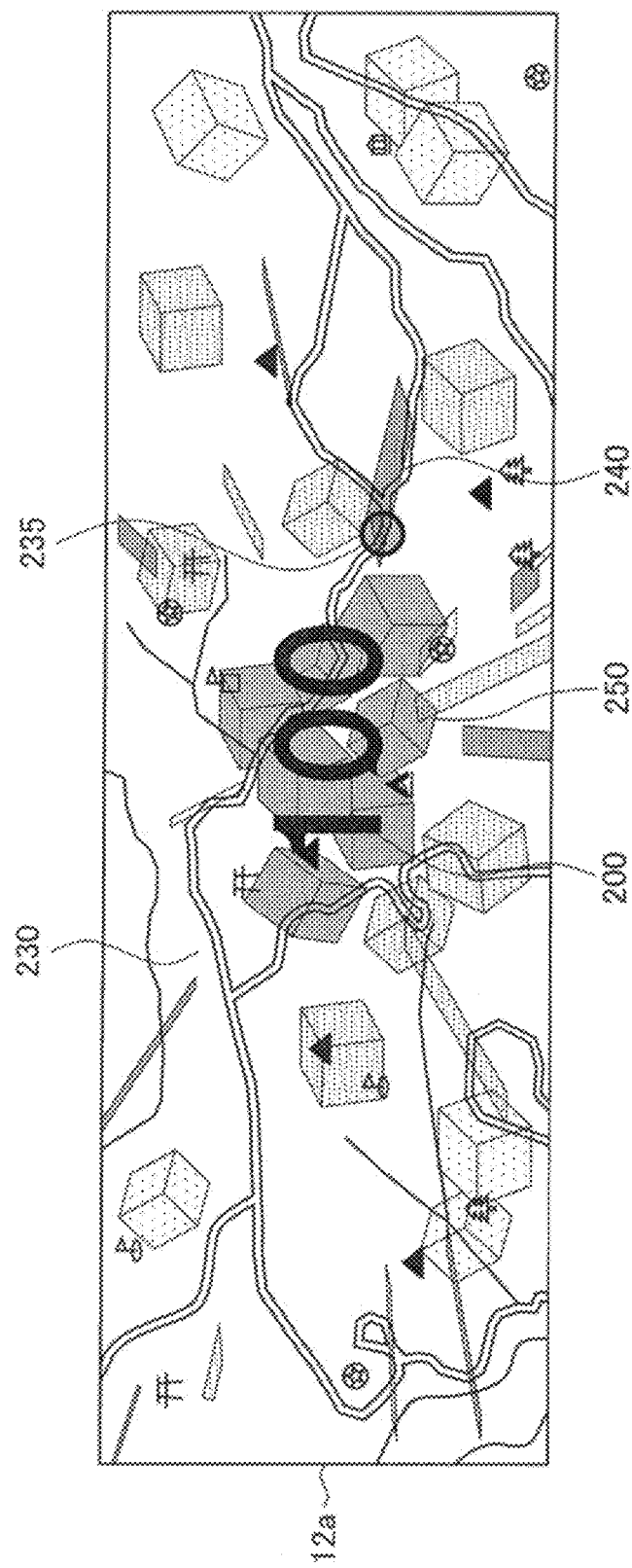
FIG. 12 is an explanatory diagram which shows an example of an image displayed on the front surface of the information processing apparatus.

FIG. 11 and FIG. 12 show another example of car navigation. FIG. 11 shows display target information displayed on the first display region 43 and the second display region 45 of the display section 40. FIG. 12 shows display target information displayed on the front surface 12*a* of the information processing apparatus 10. In this example, other than the above described vehicle speed information 200 and the rectangular images 240, box images 250 also move back and forth between the center portion and the outer edges on the near side display layer. Further, the box images 250 change color while moving. In this way, the user can more intuitively understand the vehicle speed.

Figure 13:
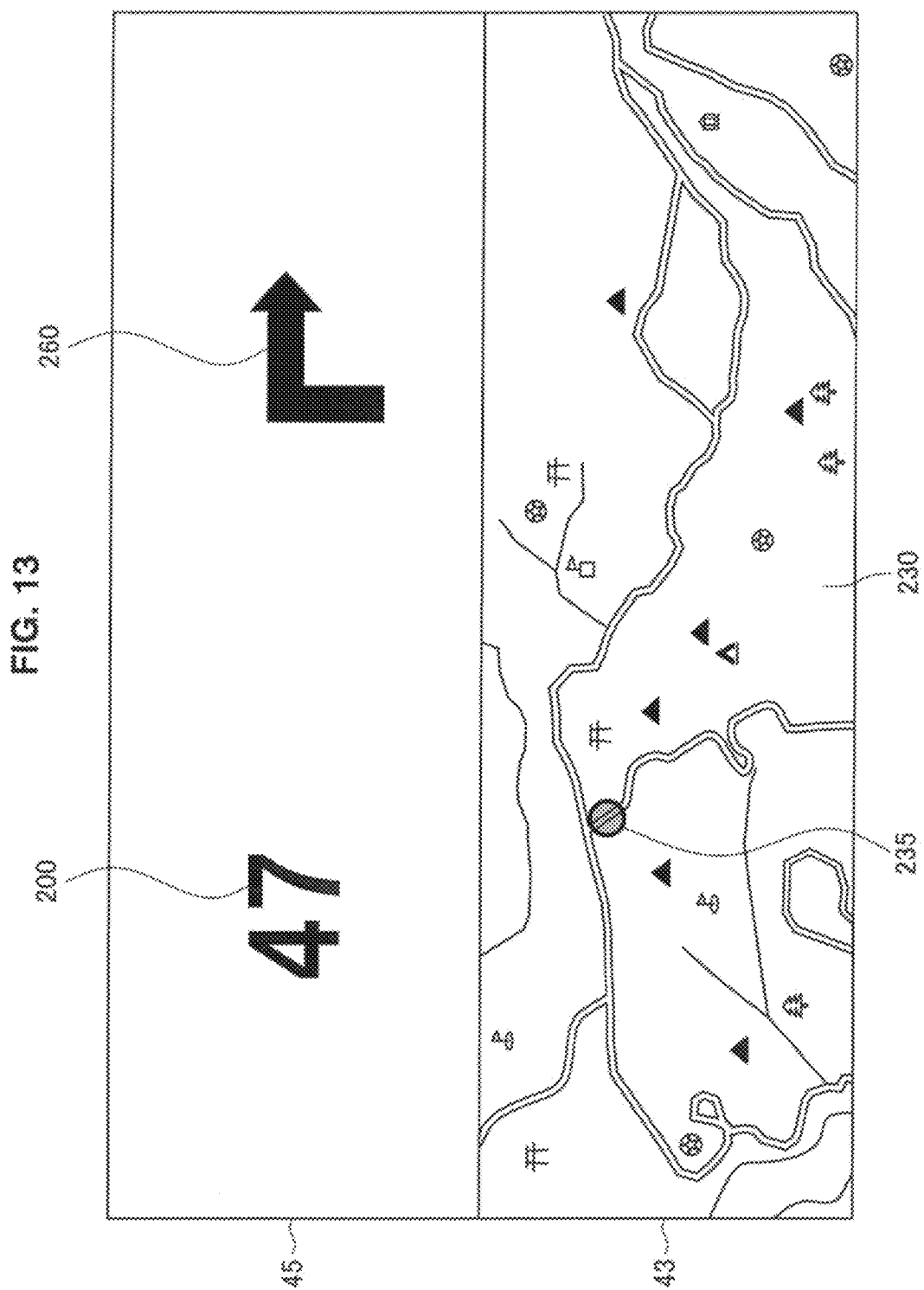
FIG. 13 is an explanatory diagram which shows an example of an image displayed on the display section.
Figure 14:
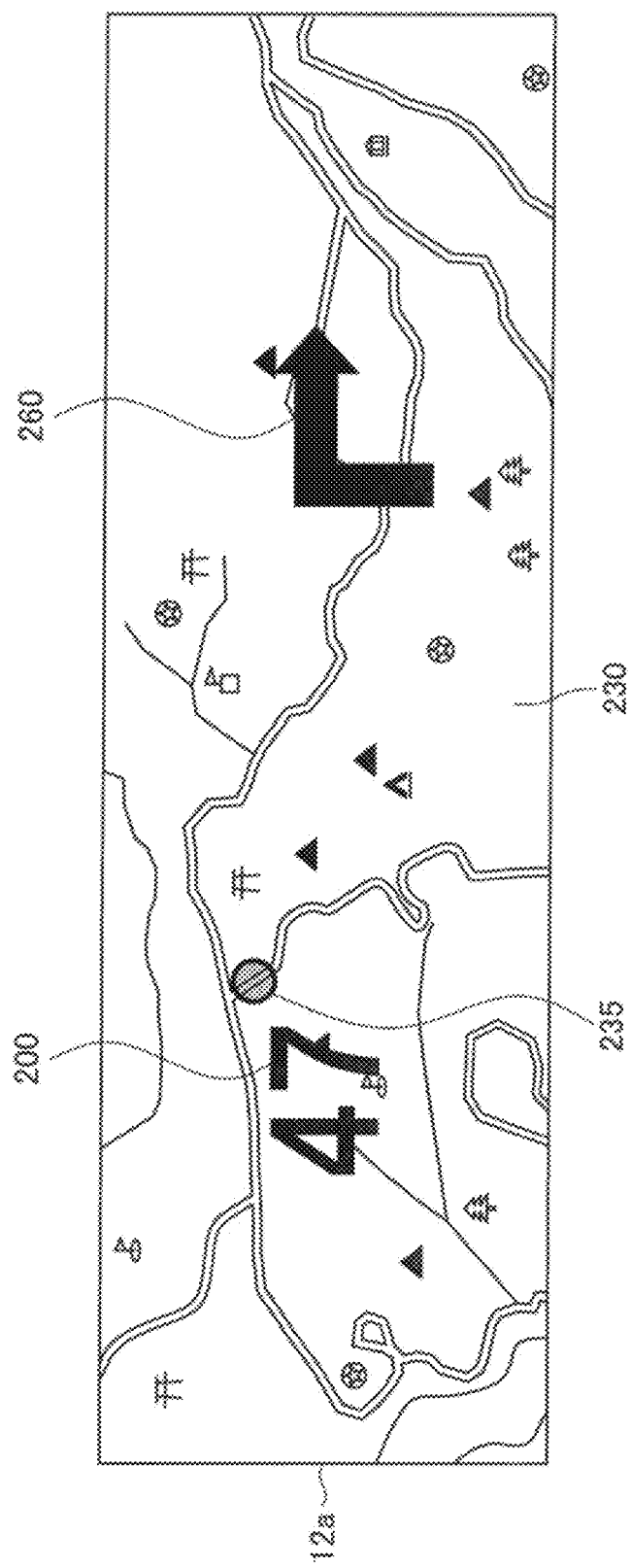
FIG. 14 is an explanatory diagram which shows an example of an image displayed on the front surface of the information processing apparatus.
Figure 15:
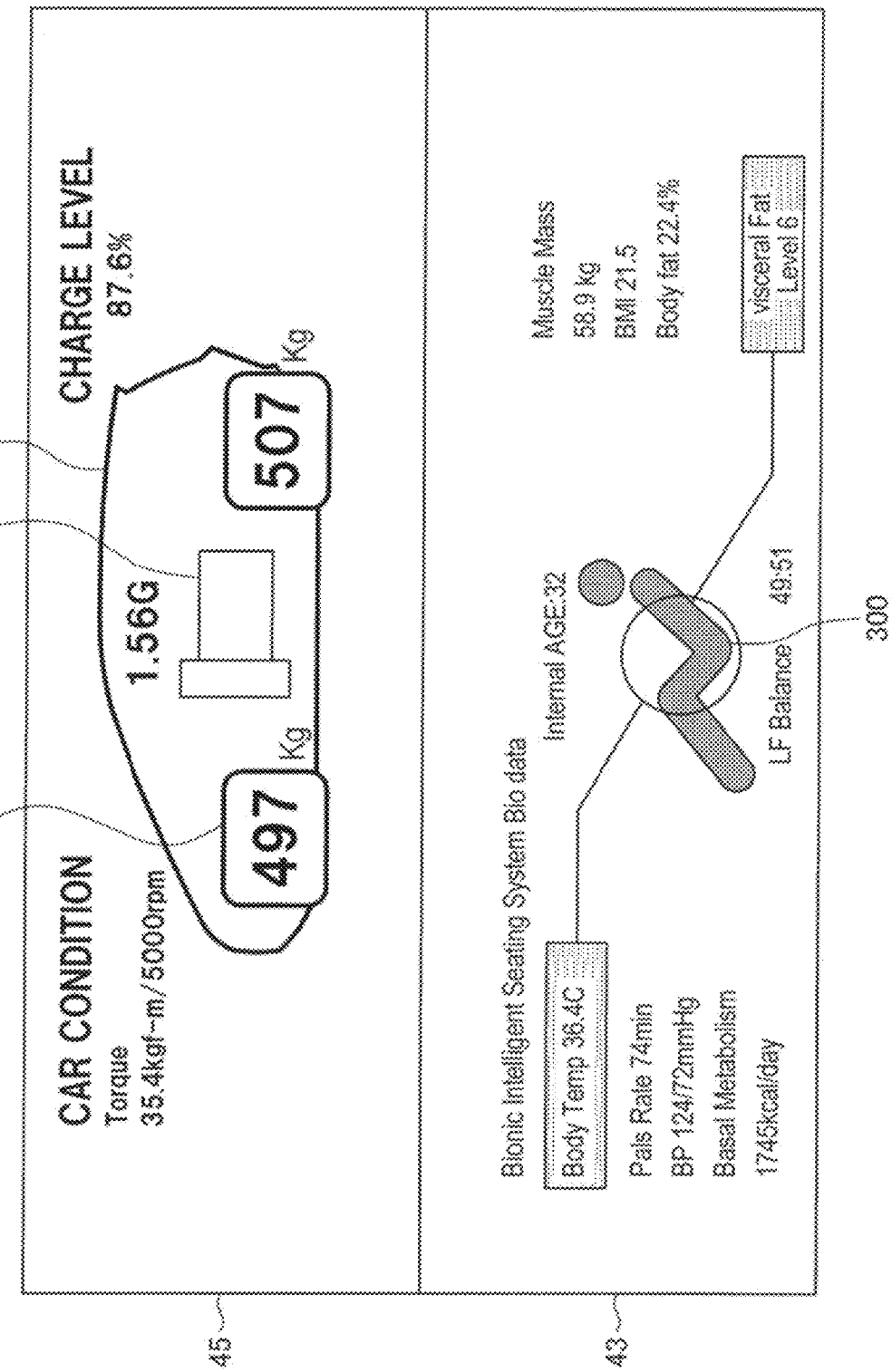
FIG. 15 is an explanatory diagram which shows an example of an image displayed on the display section.

FIG. 13 and FIG. 14 are another example of car navigation. FIG. 13 shows display target information displayed on the first display region 43 and the second display region 45 of the display section 40. FIG. 15 shows display target information displayed on the front surface 12*a* of the information processing apparatus 10.

In this example, other than the vehicle speed information 200, the display control section 104 also displays an arrow image 260, which shows the direction that the vehicle of the user is to proceed in, on the interior side display layer. The arrow image 260 may be displayed on a display layer different to that of the vehicle speed information 200. Further, the display control section 104 displays the map information 230 and the present position marker 235 on the near side display layer. In this example, the user can more intuitively understand the direction that the user himself or herself is to proceed in.
(Overlapping Display of Vital Information of the User and Vehicle Travelling Information)

Figure 16:
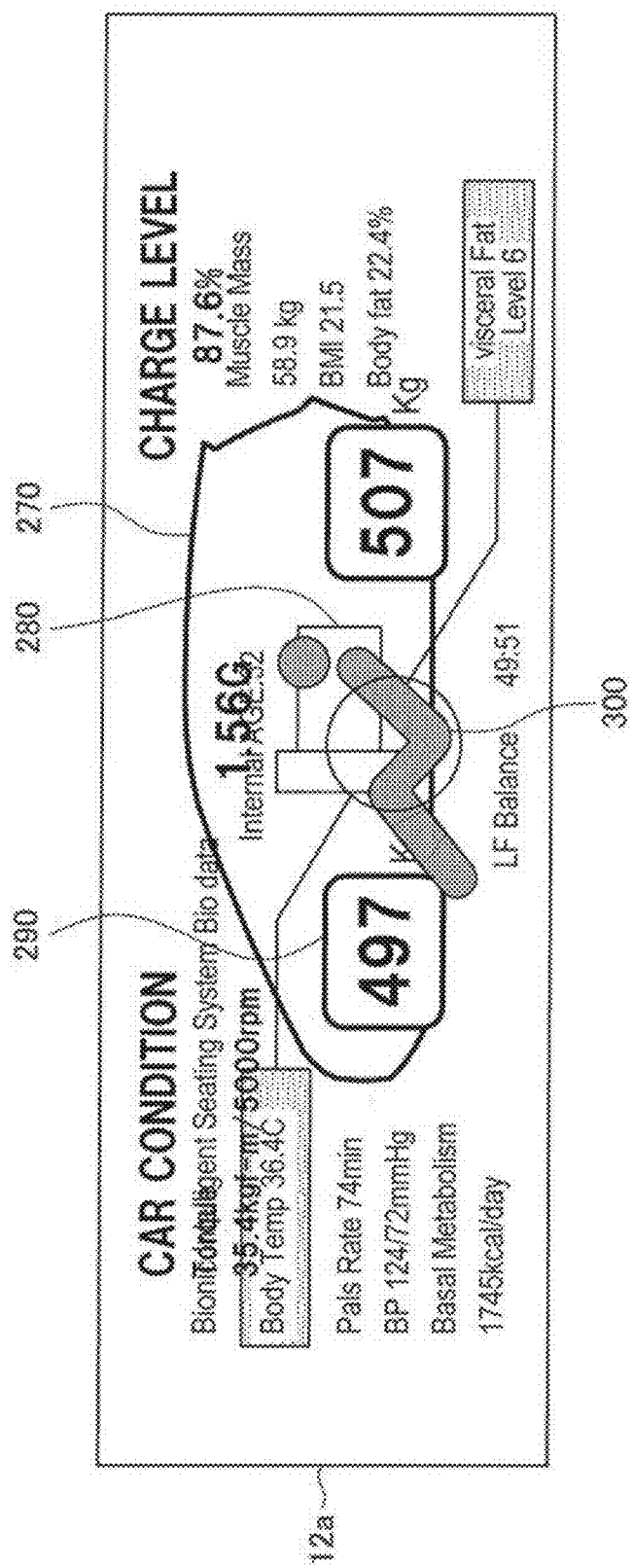
FIG. 16 is an explanatory diagram which shows an example of an image displayed on the front surface of the information processing apparatus.

Next, an example in which vital information of the user and vehicle travelling information is displayed overlapping will be described based on FIG. 15 and FIG. 16. FIG. 15 shows display target information displayed on the first display region 43 and the second display region 45 of the display section 40. FIG. 16 shows display target information displayed on the front surface 12*a* of the information processing apparatus 10.

In this example, the display control section 104 displays vehicle travelling information on the interior side display layer, and displays vital information of the user on the near side display layer. Specifically, the display control section 104 displays a vehicle body image 270 which schematically shows the vehicle body, an engine image 280 which schematically shows the engine, and images 290 which schematically show the front and rear tires. In addition, the display control section 104 displays the acceleration of the vehicle, the maximum torque/engine revolution number, the remaining fuel amount, the load applied to each of the tires or the like. It is needless to say that the display control section 104 may display information other than this as vehicle travelling information.

On the other hand, other than a person image 300 which schematically shows the user, the display control section 104 also displays the age, temperature, pulse, blood pressure, base metabolic rate, weight, BMI, body fat percentage, visceral fat level, degree of drowsiness (for example, the frequency of yawning) and a fatigue level (for example, the frequency of blinking per a unit time or the like) of the user. It is needless to say that the display control section 104 may display information other than this as vital information.

According to this example, the user can simultaneously understand the vital information of the user himself or herself and the vehicle travelling information. Note that, while the priority of the vital information is higher than the priority of the vehicle travelling information in the example of FIG. 15, the display control section 104 may adjust the priorities of each type of information based on operations of the user or the like, and may switch the display layers of each type of information. Note that, for example, a sensor capable of detecting this vital information may be worn by the user, and the vital information may be acquired from this sensor. Further, the content of the vehicle travelling information may be changed in accordance with the vital information of the user, and in this case, the user can easily understand how the vehicle travelling information has been changed by changes in the vital information of the user himself or herself. The display control section 104 may display the changed vehicle travelling information in a state different to that of other vehicle travelling information (luminance, color or the like). Further, the display control section 104 may selectively display information which the user has touched, from among of the vehicle travelling information displayed on the interior side display layer, on the near side display layer. The display control section 104 may perform processes similar to the case where the vital information is displayed on the interior side display layer. That is, the display control section 104 may selectively display information which the user has touched, from among the vital information displayed on the interior side display layer, on the near side display layer.
(Overlapping Display of Captured Images of the Rear of a Vehicle and Indication Images)

Figure 17:
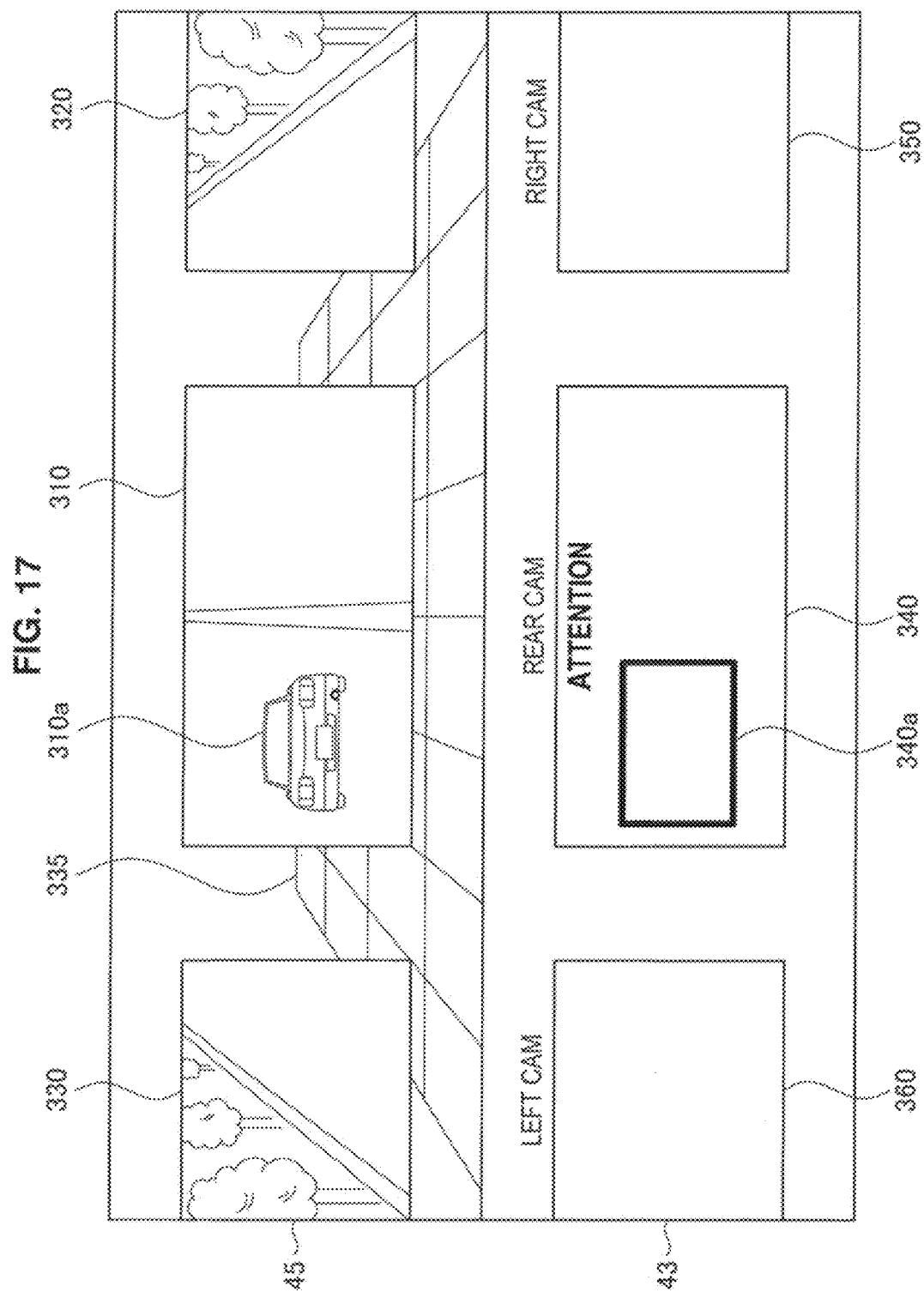
FIG. 17 is an explanatory diagram which shows an example of an image displayed on the display section.
Figure 18:
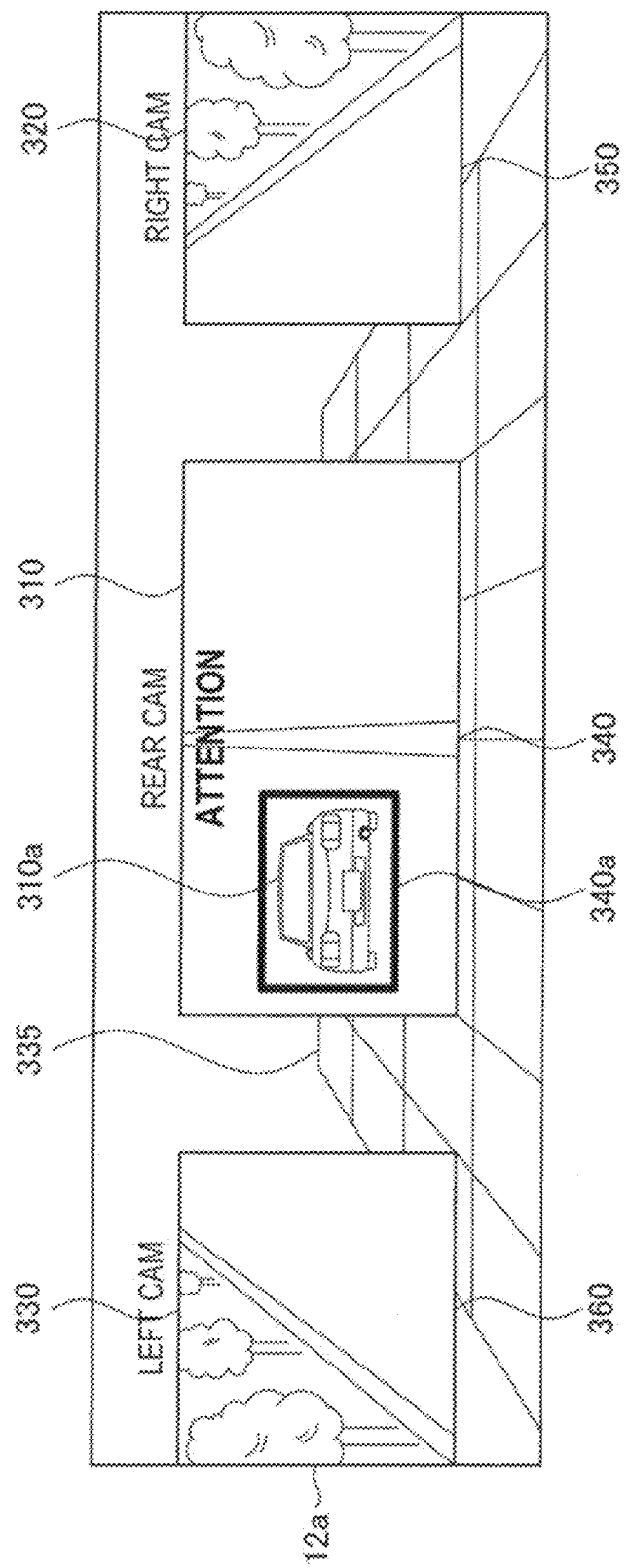
FIG. 18 is an explanatory diagram which shows an example of an image displayed on the front surface of the information processing apparatus.
Figure 19:
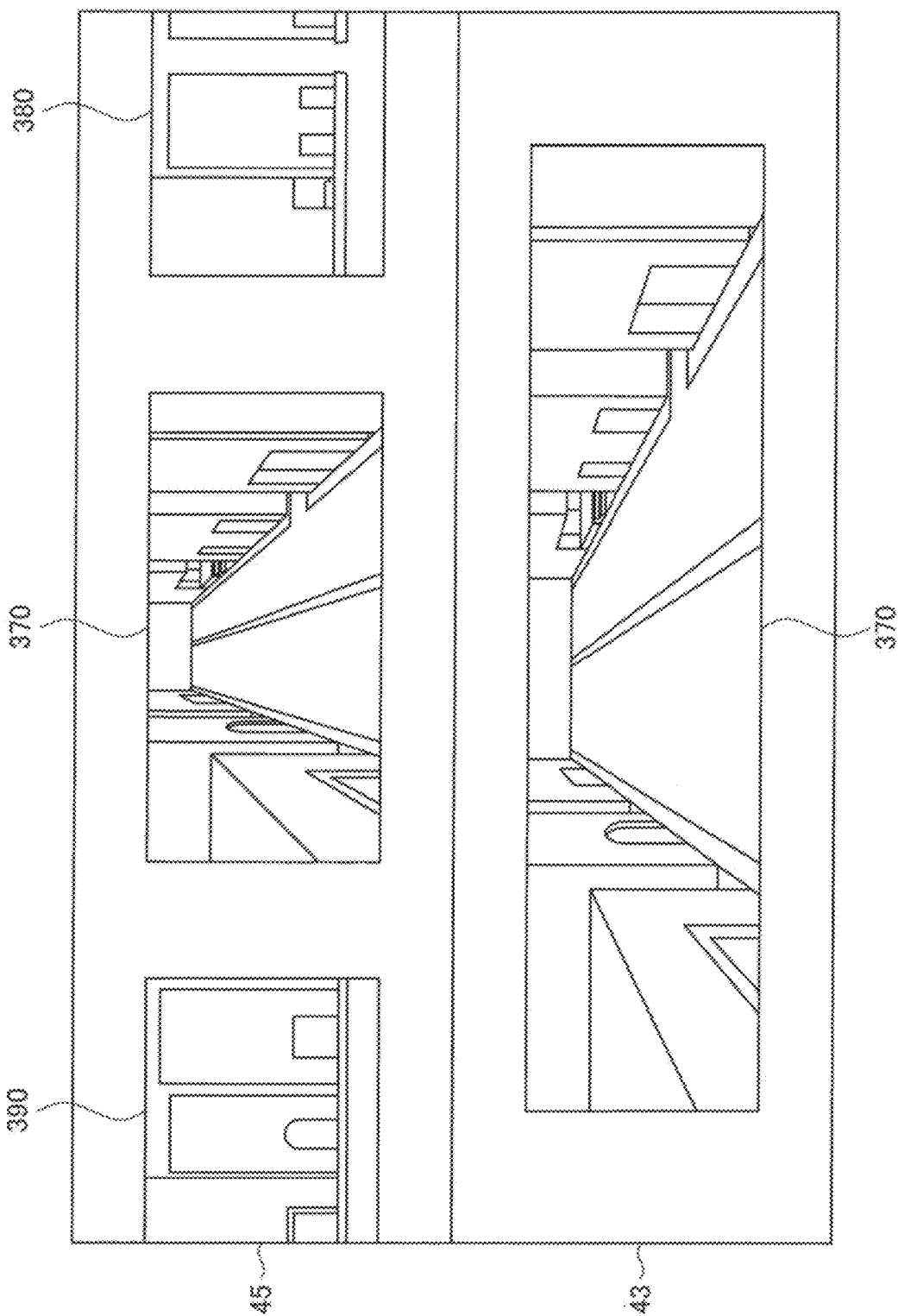
FIG. 19 is an explanatory diagram which shows an example of an image displayed on the display section.

Next, an example in which captured images of the rear of a vehicle and indication images are displayed overlapping will be described based on FIG. 17 and FIG. 18. FIG. 17 shows display target information displayed on the first display region 43 and the second display region 45 of the display section 40. FIG. 18 shows display target information displayed on the front surface 12a of the information processing apparatus 10. Note that, an imaging apparatus which images directly behind the vehicle, an imaging apparatus which images the right rear, and an imaging apparatus which images the left rear are included in this example. Also, the captured images captured by each of the imaging apparatuses are input to the display control section 104.

The display control section 104 displays a captured image 310 of directly behind the vehicle on the central portion of the interior side display layer, displays a captured image 320 of the vehicle right rear on the right side portion, and displays a captured image 330 of the vehicle left rear on the left side portion. Further, in order to show that the vehicle is travelling, the display control section 104 displays a lattice image 335 extending from the central portion of the interior side display layer to the lower edge portion of the interior side display layer, and moves this lattice image 335 in the lower edge portion direction of the interior side display layer. Note that, in this example, a vehicle 310a which is looking to overtake the vehicle of the user is drawn in the captured image 310.

The display control section 104 displays a framed image 340 which encloses the captured image 310 on the central portion of the near side display layer, displayed a framed image 350 which encloses the captured image 320 on the right side portion, and displays a framed image 360 which encloses the captured image 330 on the left side portion. Further the display control section 104 displays an indication image (for example, a framed image drawn by a red line) 340a, which shows a target, that is, the vehicle 310a, to be visually recognized by the user, overlapping the vehicle 310a within the captured image 310. In this way, the user can easily understand a target to be visually recognized by the user himself or herself. Note that, the display control section 104 may switch the display layers of each type of display target information, based on operations of the user or the like. Further in the case where the fatigue level or drowsiness of the user is high, or in the case of traveling at night, the display control section 104 may switch the captured images to night vision.

(Overlapping Display of Captured Images of in Front of a Vehicle and a Specific Captured Image or the Like)

Next, an example in which captured images of in front of a vehicle and a specific captured image or the like are displayed overlapping will be described based on FIG. 19 to FIG. 22. FIG. 19 to FIG. 22 show display target information displayed on the first display region 43 and the second display region 45 of the display section 40. Note that, an imaging apparatus which images directly in front of the vehicle, an imaging apparatus which images the right side, and an imaging apparatus which images the left side are included in this example. Also, the captured images captured by each of the imaging apparatuses are input to the display control section 104.

The display control section 104 displays a captured image 370 of directly in front of the vehicle on the central portion of the interior side display layer, displays a captured image 380 of the vehicle right side on the right side portion, and displays a captured image 390 of the vehicle left side on the left side portion. Further, in order to show that the vehicle is travelling, the display control section 104 displays a lattice image 335 extending from the central portion of the interior side display layer to the lower edge portion of the interior side display layer, and may move this lattice image 335 in the lower edge portion direction of the interior side display layer.

Figure 20:
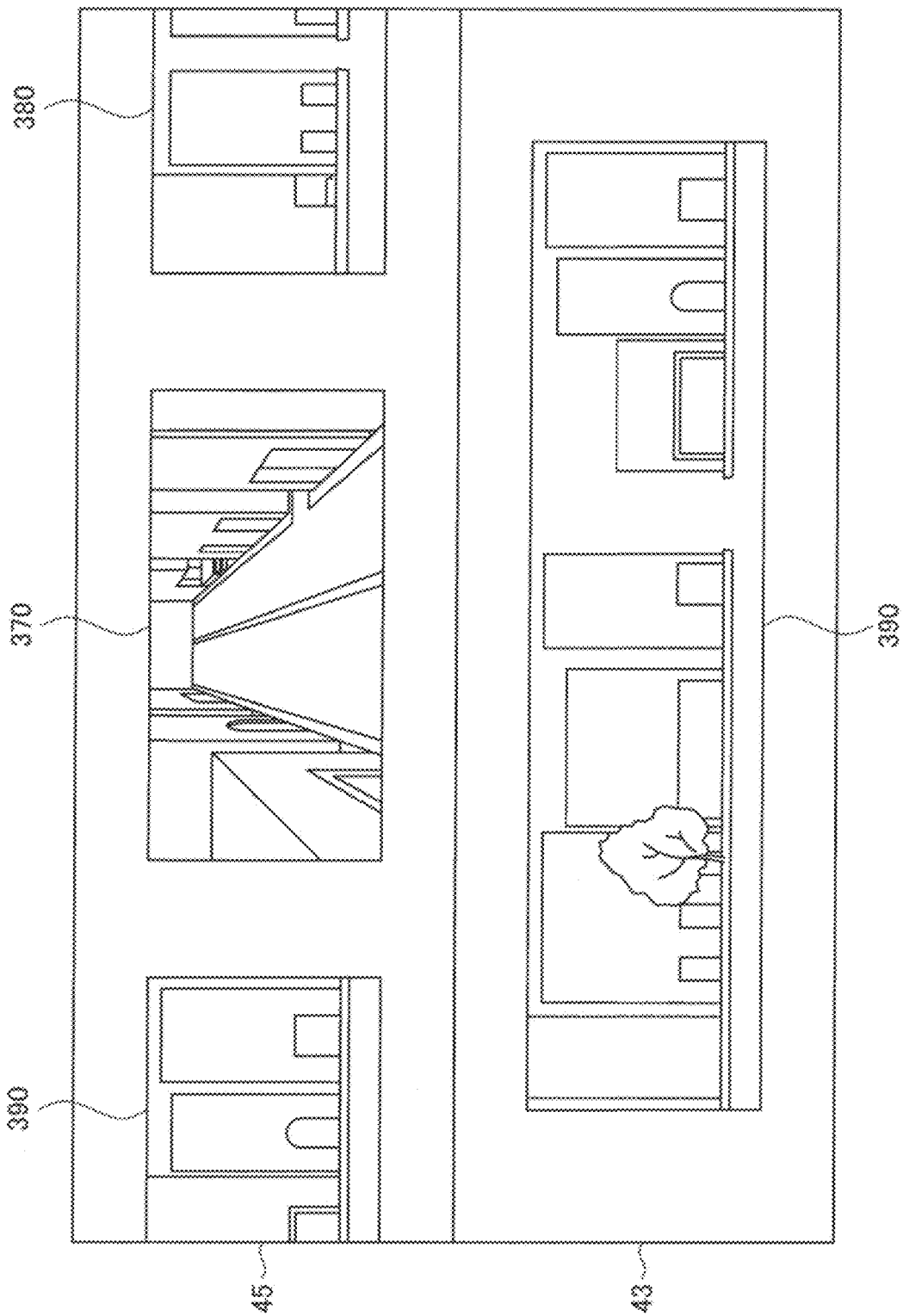
FIG. 20 is an explanatory diagram which shows an example of an image displayed on the display section.

The display control section 104 displays a captured image 370 on the near side display layer. That is, in this case, the priority of the captured image 370 is higher than the priority of the other captured images. For example, in the case where the user turns his or her face towards the left side, the display control section 104 may display the captured image 390 on the near side display layer, such as shown in FIG. 20. In this case, since the captured image of the left side may be necessary for the user, the priority of the captured image 390 becomes higher than the priority of the other captured images. For example, in the case where the user performs an operation of swiping a hand to the left side, the display control section 104 may perform similar switching. Further, in the case where the user touches the captured image 390, the display control section 104 may perform a similar process. It is possible to determine that the user has touched the captured image 390 by operation information from the touch panel 100. The display control section 104 may perform a similar process related to the captured image 380. In this way, the user can visually recognize a desired captured image at a desired timing.

Figure 21:
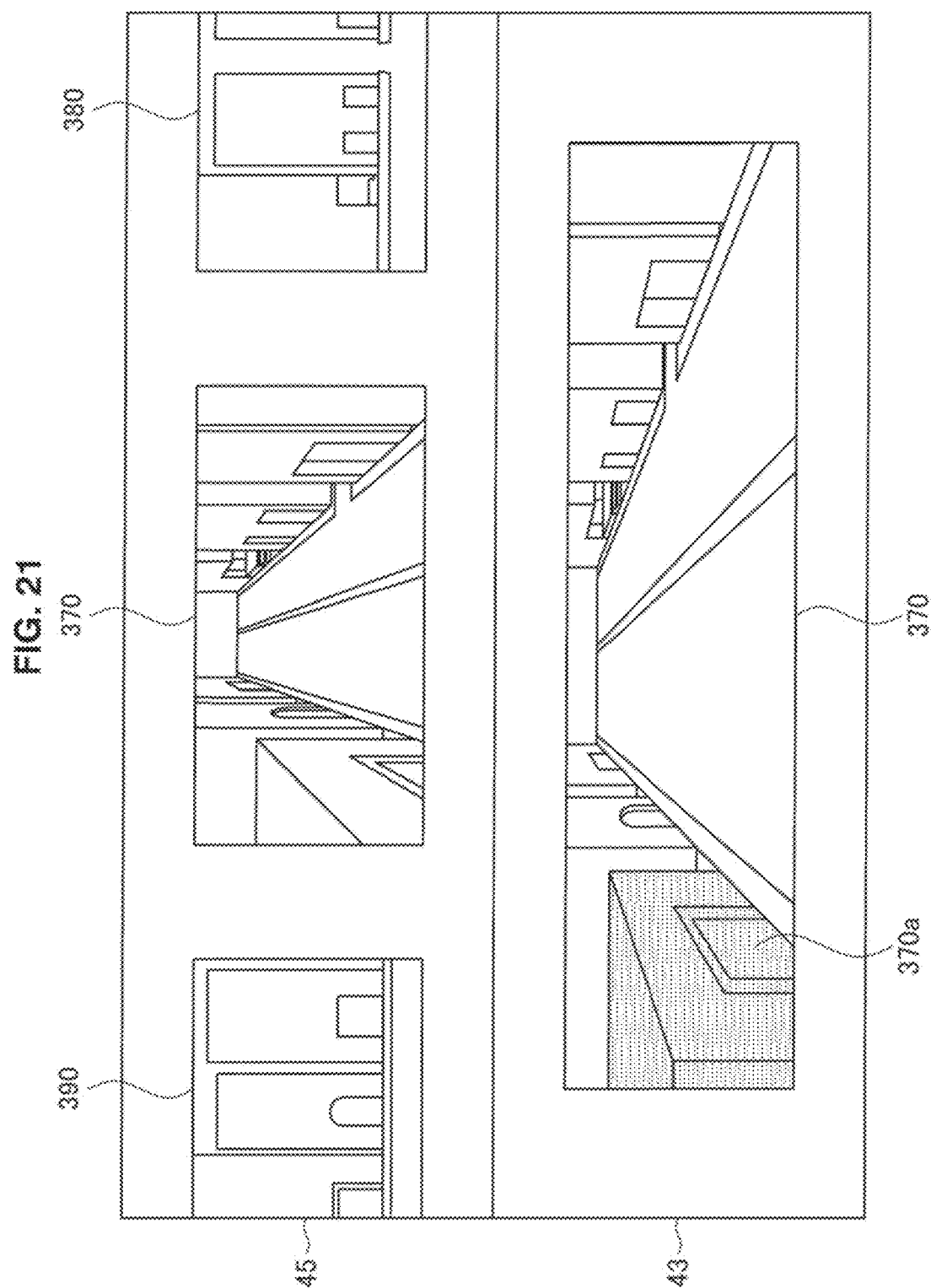
FIG. 21 is an explanatory diagram which shows an example of an image displayed on the display section.

Further, the display control section 104 may highlight an object within a captured image based on various factors. For example, in the case where the remaining fuel amount of the vehicle has decreased, the display control section 104 may highlight a gas station 370a within the captured image, such as shown in FIG. 21. In particular, in the case where the vehicle is an electric vehicle, since gas stations acceptable for the electric vehicle will be limited, the effect according to this process will be significant.

Figure 22:
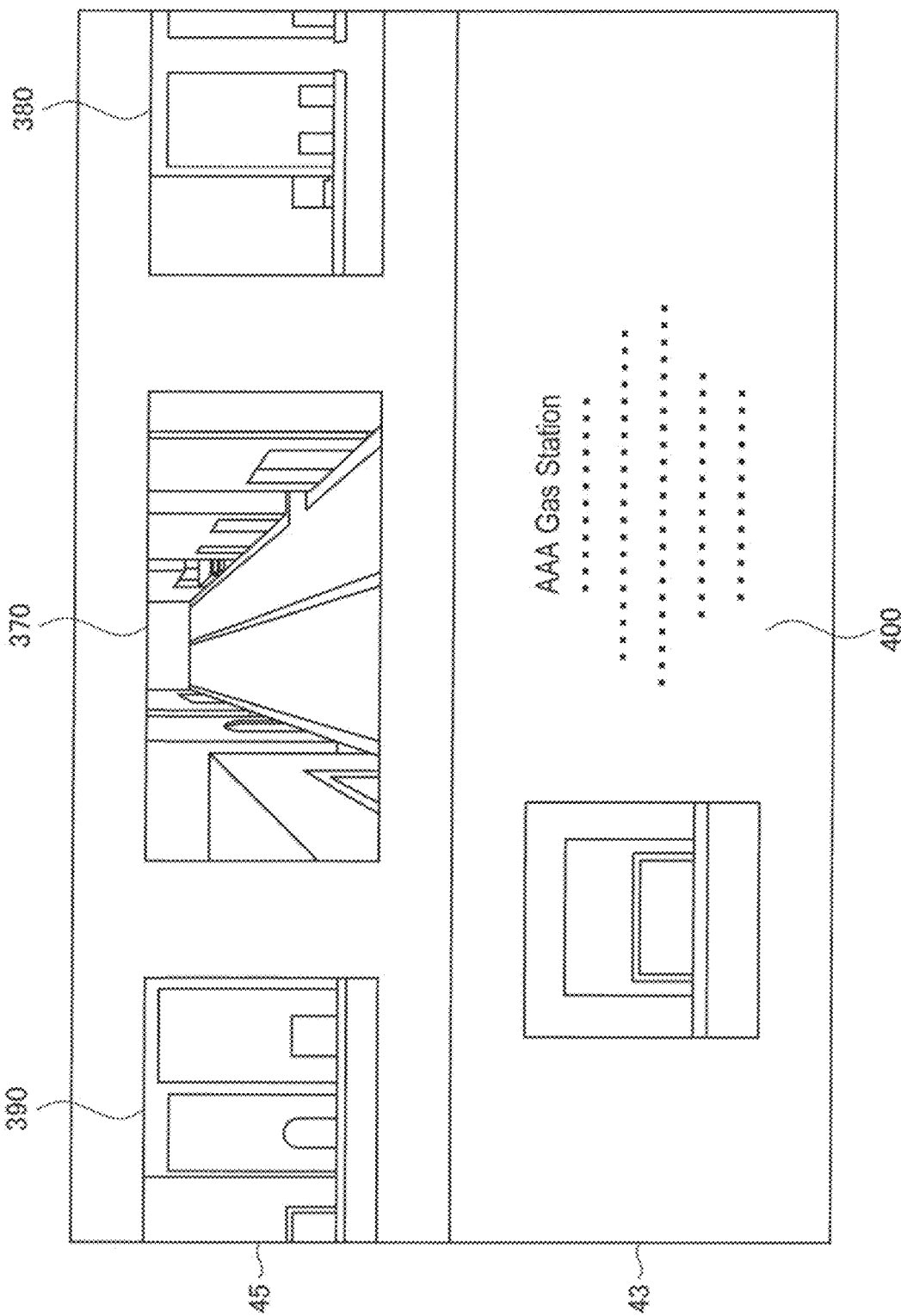
FIG. 22 is an explanatory diagram which shows an example of an image displayed on the display section.

Further, the display control section 104 may highlight a restaurant at lunch time, and may highlight respectively different objects while commuting or during leisure. For example, a convenience store may be highlighted while commuting, and leisure facilities may be highlighted during leisure. Further, the display control section 104 may not only simply highlight objects, but may also display the objects on the near side display layer. Here, as shown in FIG. 22, the display control section 104 may not only simply display objects on the near side display layer, but may also display object-related information 400 related to these objects (information such as a photograph, the name, or the address of the gas station in the example of FIG. 22).

Further, in the case where the vehicle passes a specific object within a captured image, it is possible to perform a process which is said to perform a specific process (play music or the like). The specific object may not actually exist. For example, the display control section 104 displays some object (for example, a CD) within the captured image, and in the case where the vehicle passes this object, a specific process (playing specific music or the like) may be performed.

Further, highlighting may also be performed on the interior side display layer. For example, in the case of transitioning from the state of FIG. 21 to the state of FIG. 20, the display control section 104 may highlight a gas station 370a in the captured image 370 within the interior side display layer. Further, the display control section 104 may display captured images captured at a position at which the vehicle is estimated to arrive, instead of captured images of the vehicle surroundings, by a method similar to the above described method. In this case, the display control section 104 may estimate a position at which the vehicle will pass based on a vehicle travelling direction, a destination set by the user or the like, and may acquire captured images captured at this position from a network. In this case, the display control section 104 is implemented by imaging with captured images in which a destination is arrived at by passing the present position of the user.

(Overlapping Display of Captured Images of in Front of a Vehicle and an Indication Image)

Figure 23:
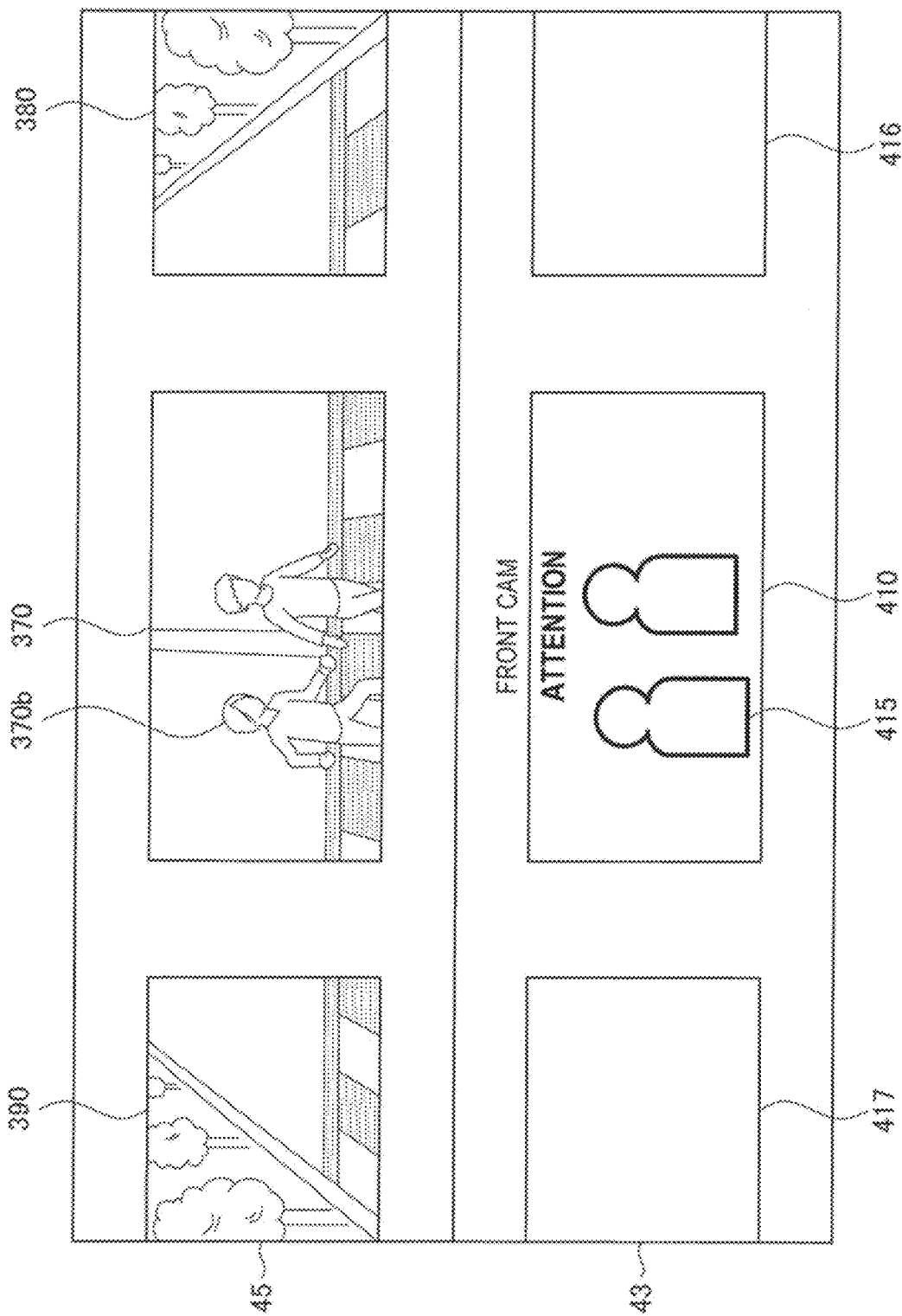
FIG. 23 is an explanatory diagram which shows an example of an image displayed on the display section.
Figure 24:
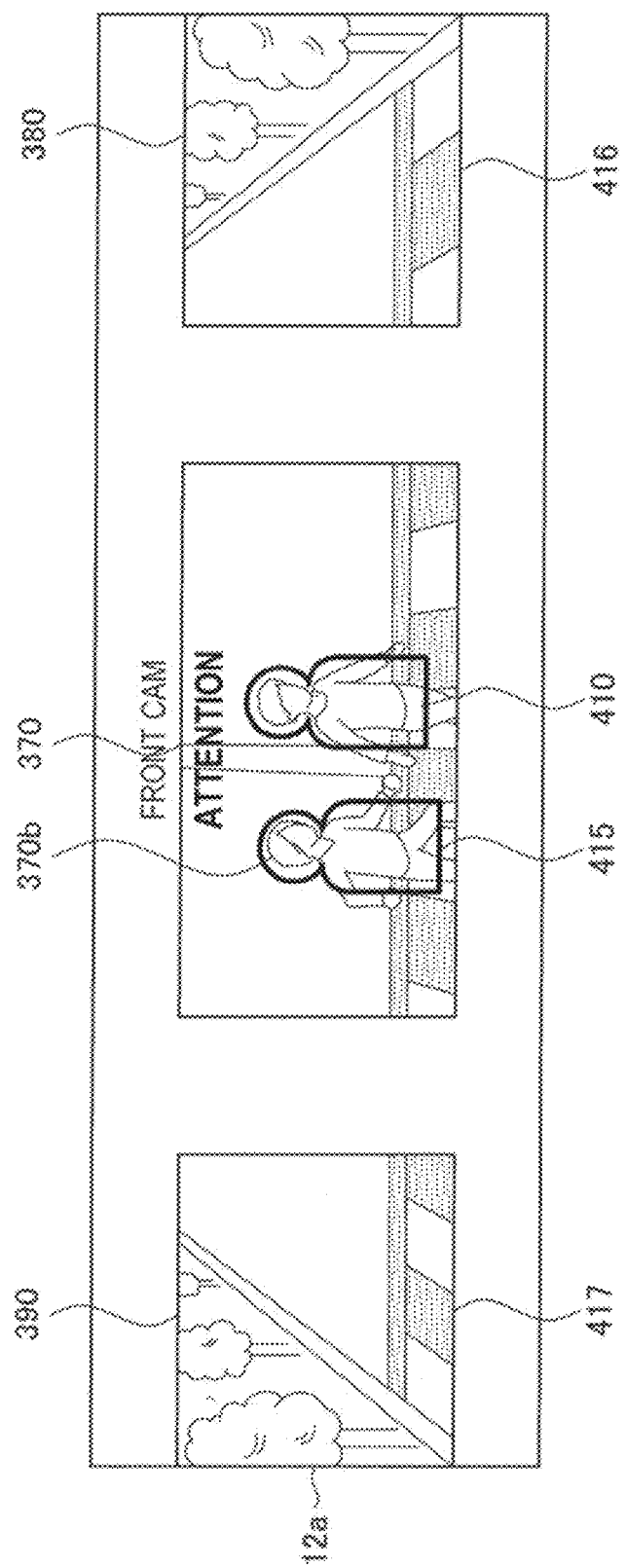
FIG. 24 is an explanatory diagram which shows an example of an image displayed on the display section.

Next, an example in which captured images of in front of a vehicle and an indication image are displayed overlapping will be described based on FIG. 23 and FIG. 24. FIG. 23 shows display target information displayed on the first display region 43 and the second display region 45 of the display section 40. FIG. 24 shows display target information displayed on the front surface 12a of the information processing apparatus 10. Note that, an imaging apparatus which images directly in front of the vehicle, an imaging apparatus which images the right side, and an imaging apparatus which images the left side are included in this example. Also, the captured images captured by each of the imaging apparatuses are input to the display control section 104.

The display control section 104 displays a captured image 370 of directly in front of the vehicle on the central portion of the interior side display layer, displays a captured image 380 of the vehicle right side on the right side portion, and displays a captured image 390 of the vehicle left side on the left side portion. Further, in order to show that the vehicle is travelling, the display control section 104 displays a lattice image 335 extending from the central portion of the interior side display layer to the lower edge portion of the interior side display layer, and may move this lattice image 335 in the lower edge portion direction of the interior side display layer. Note that, in this example, a person 370b who is crossing in front of the vehicle of the user is drawn on the captured image 310.

The display control section 104 displays a framed image 410 which encloses the captured image 370 on the central portion of the near side display layer, and displays an indication image (for example, a framed image drawn by a red line) 415, which shows a target, that is, the person 370b, to be visually confirmed by the user, overlapping the person 370b within the captured image 370. In this way, the user can easily understand the target to be visually confirmed by the user himself or herself. Note that, the display control section 104 may switch the display layers of each type of display target information, based on operations of the user or the like. Further, in the case where a fatigue level or drowsiness of the user is high, or in the case of travelling at night, the display control section 104 may switch the captured images to navigation. The display control section 104 may display framed images 416 and 417 which enclose other captured images 380 and 390.

(Exchange of Messages Between Users)

Figure 25:
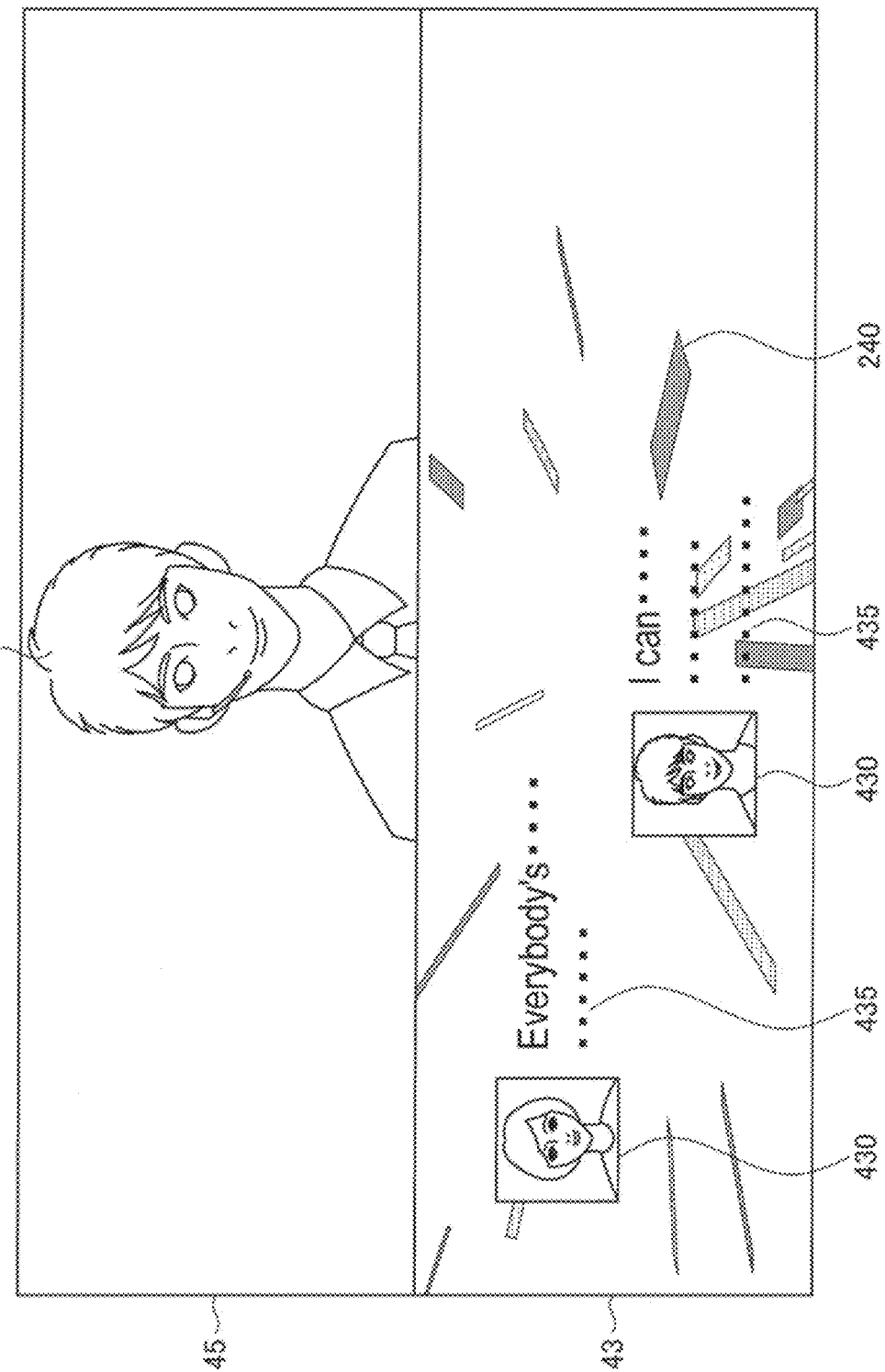
FIG. 25 is an explanatory diagram which shows an example of an image displayed on the display section.
Figure 26:
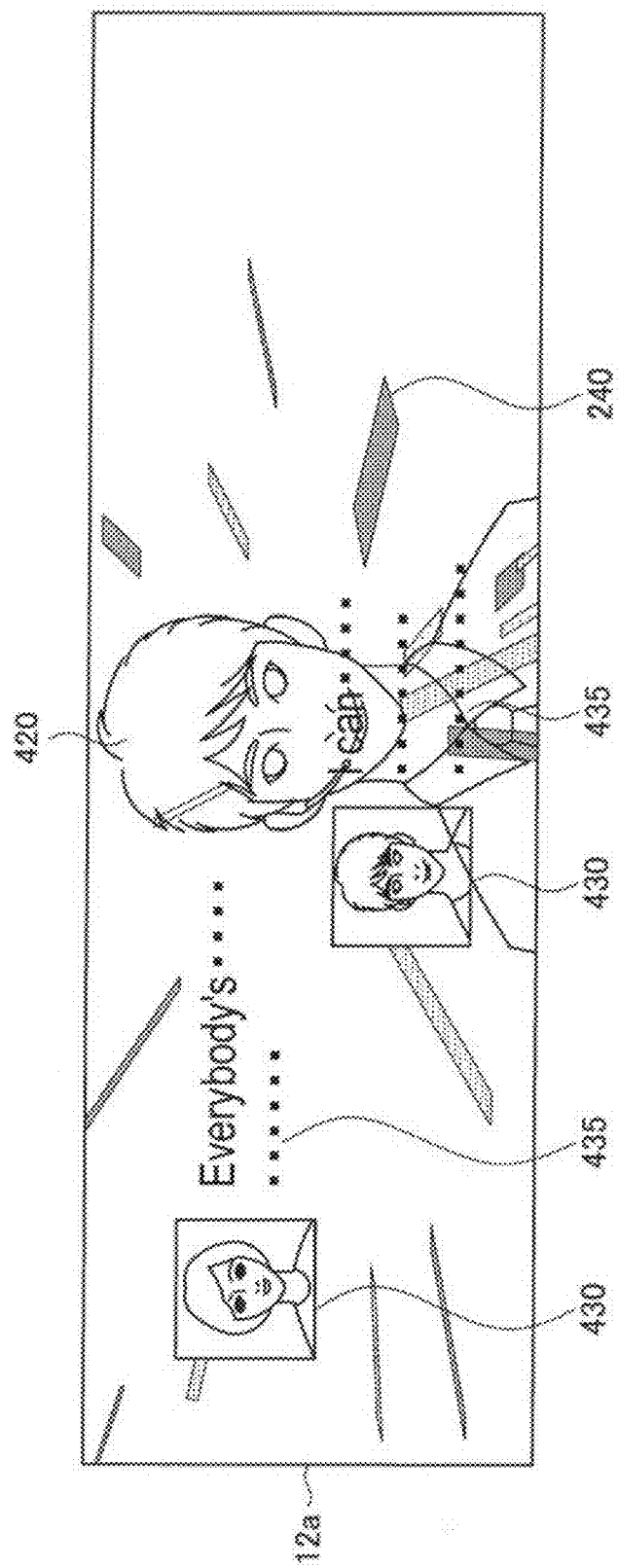
FIG. 26 is an explanatory diagram which shows an example of an image displayed on the front surface of the information processing apparatus.

Next, an example in which an exchange of messages between users is performed will be described based on FIG. 25 and FIG. 26. FIG. 25 shows display target information displayed on the first display region 43 and the second display region 45 of the display section 40. FIG. 26 shows display target information displayed on the front surface 12a of the information processing apparatus 10. Note that, in this example, a microphone is included in the vehicle, and the user can input messages by using the microphone. The messages input from the user are converted into text by the display control section 104, and are transmitted to other users from the communication section 101. The communication section 101 receives messages from the other users (may be text data or may be audio data) and captured images of the other users, and outputs the received messages and captured images to the display control section 104.

The display control section 104 displays a message 435 of a user and an icon 430 which shows the user on the near side display layer in a time series. For example, the display control section 104 displays the messages directly after being received on the lower edge of the near side display layer, and afterwards moves the messages in an upper direction. In this case, the vertical direction of the near side display layer is a time axis. Further, the display control section 104 may display the messages directly after being received on the outside edge of the near side display layer, and afterwards move the messages towards the central portion of the near side display layer while being reduced. In this case, the depth direction of the near side display layer is a time axis. Further, the display control section 104 may display messages on the near side display layer only when the messages are received.

The display control section 104 may perform display together with the above described rectangular images 240 on the near side display layer. The display control section 104 displays captured images of other users who are exchanging messages with the user on the interior side display layer. In this way, the user can actually sense having conversations with the other users. Other display target information (for example, map information or the like) may be displayed on the interior side display layer. In the case where some spot (for example, a building, amusement park or the like) appears during a conversation, the display control section 104 may retrieve the position of this spot and a route up to this route, and may display this position and route on the interior side display layer (start of navigation).

(Notification that the User is Directed Towards a Destination)

Figure 27:
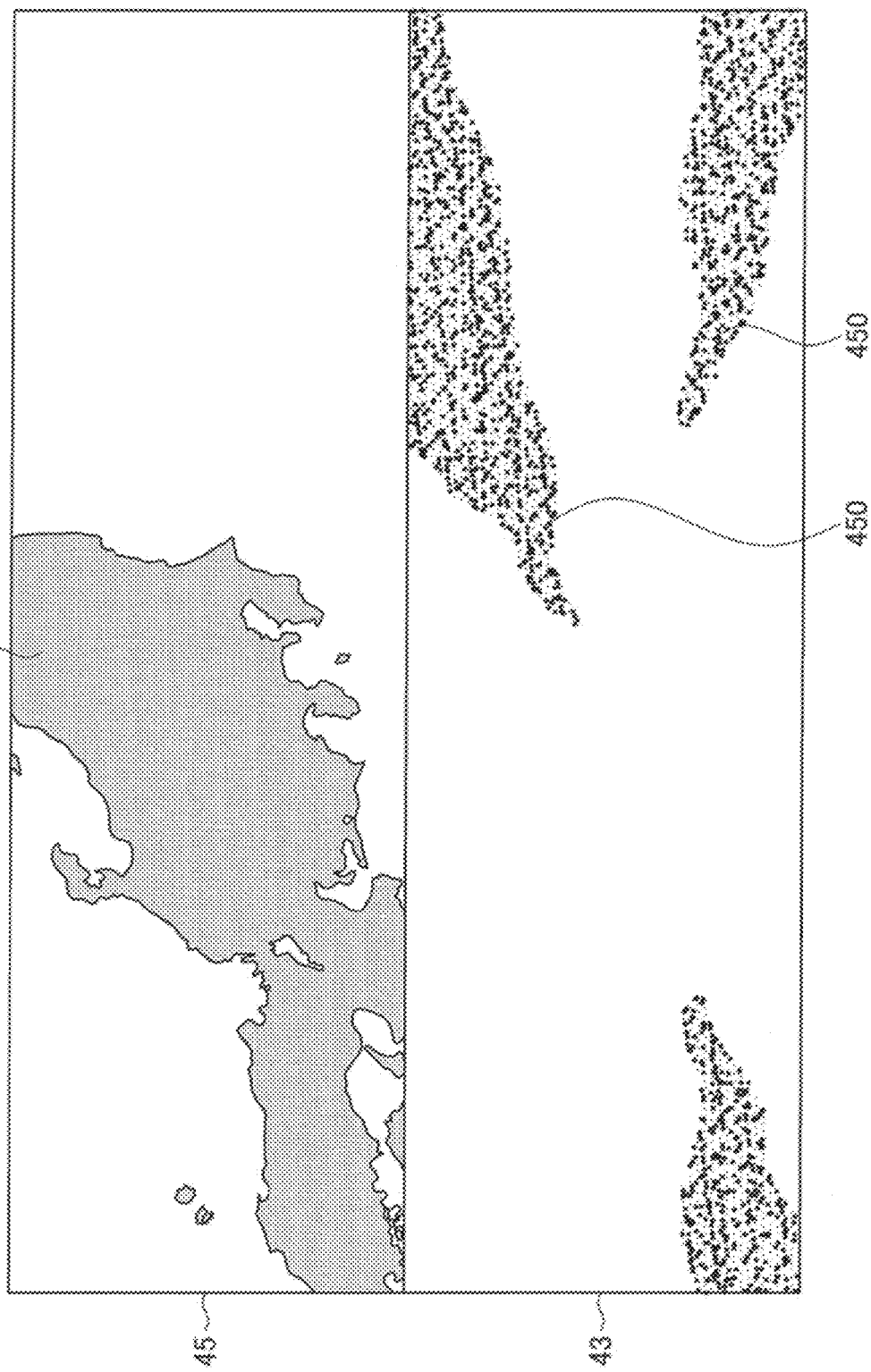
FIG. 27 is an explanatory diagram which shows an example of an image displayed on the display section.
Figure 28:
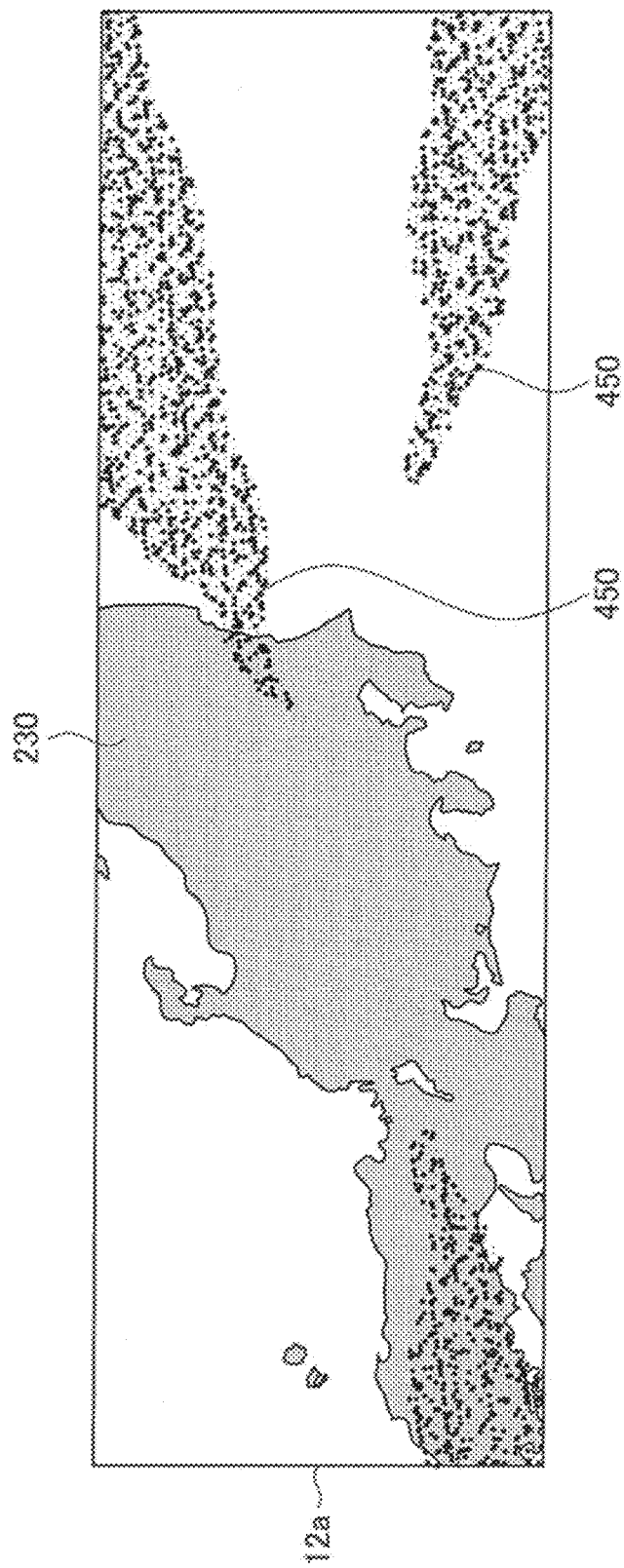
FIG. 28 is an explanatory diagram which shows an example of an image displayed on the front surface of the information processing apparatus.
Figure 29:
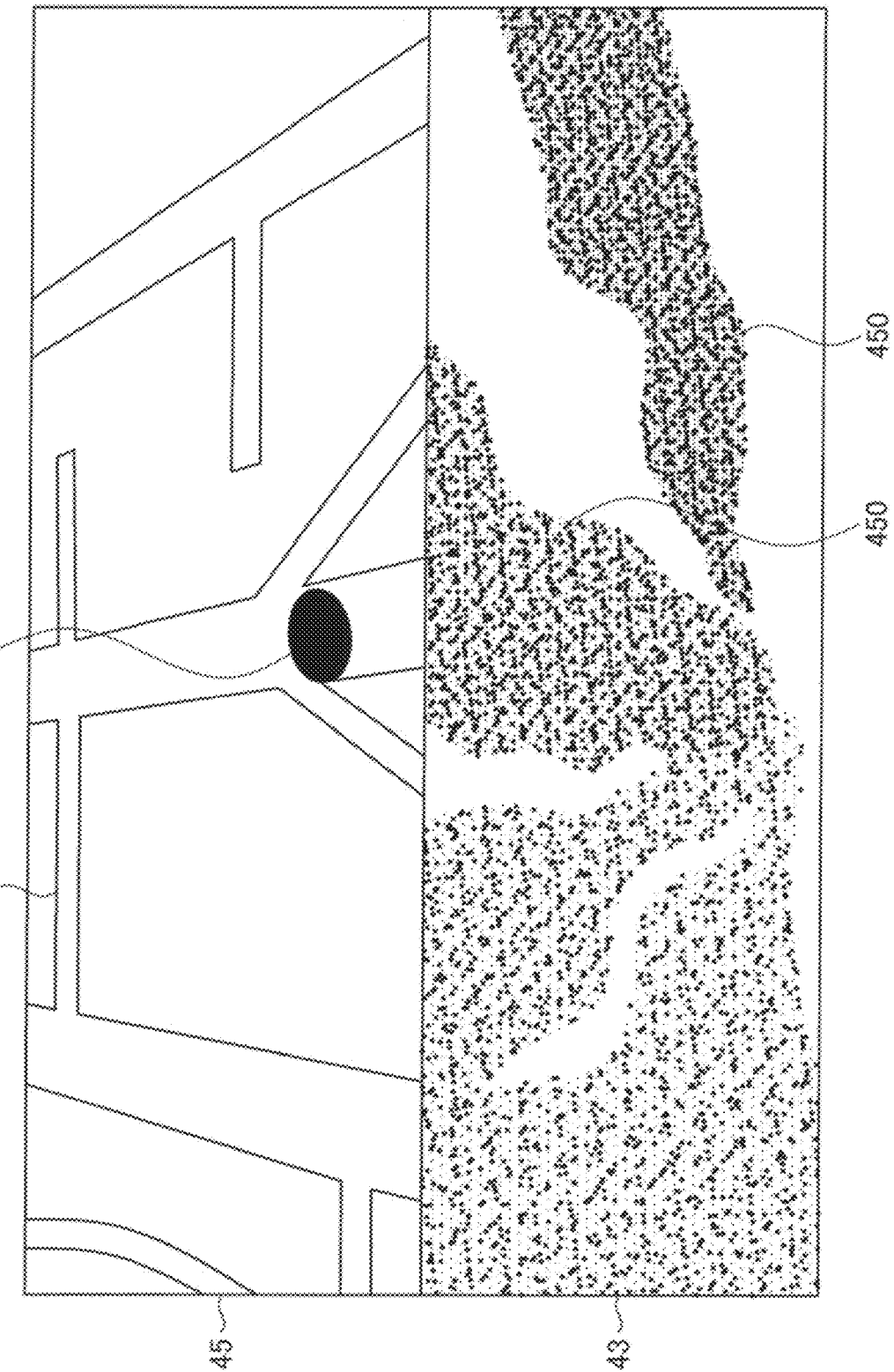
FIG. 29 is an explanatory diagram which shows an example of an image displayed on the display section.
Figure 30:
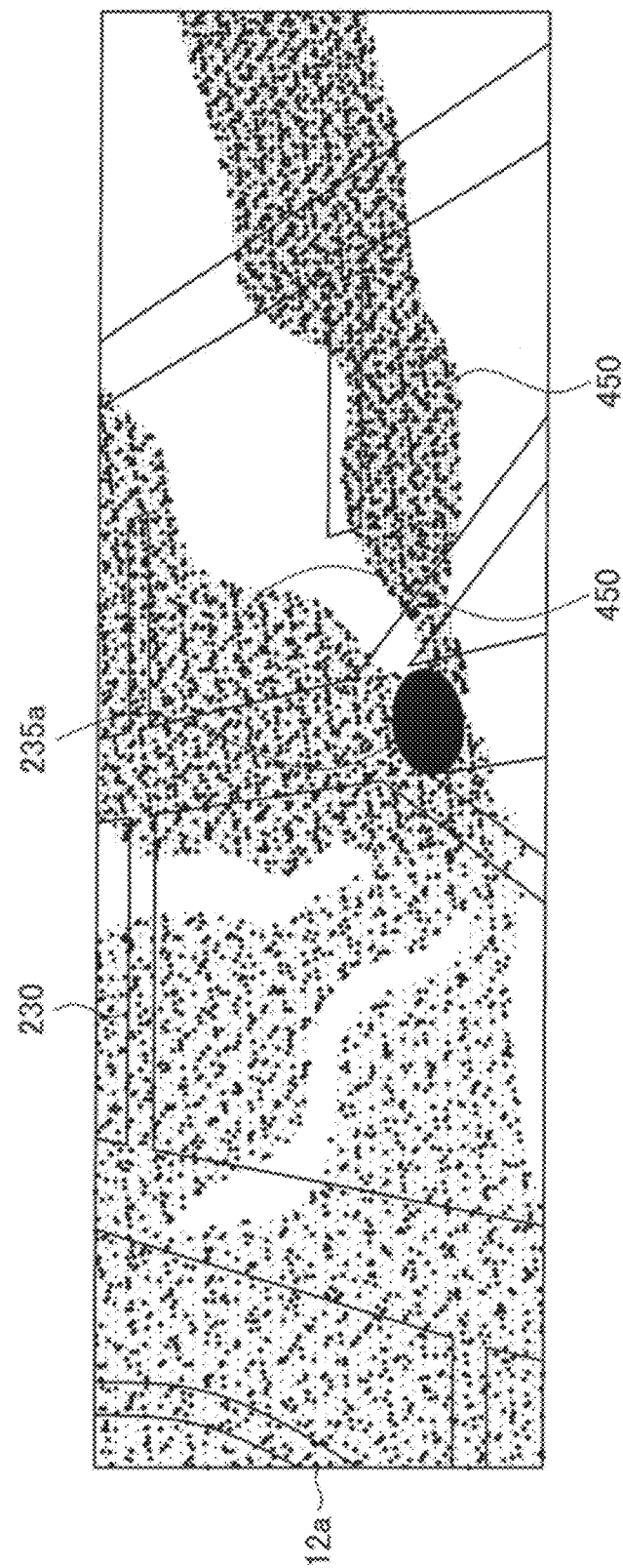
FIG. 30 is an explanatory diagram which shows an example of an image displayed on the front surface of the information processing apparatus.

Next, an example in which notification is performed that the user is directed towards a destination will be described based on FIG. 27 to FIG. 30. FIGS. 27 and 29 show display target information displayed on the first display region 43 and the second display region 45 of the display section 40. FIGS. 28 and 30 shows display target information displayed on the front surface 12a of the information processing apparatus 10.

As shown in FIG. 27 to FIG. 30, the display control section 104 displays map information 230, which shows all of Japan, on the interior side display layer, and enlarges the map information 230 as the user approaches the destination. The display control section 104 eventually displays a destination marker 235a near the central portion of the interior side display layer. On the other hand, the display control section 104 displays band images 450 constituted of a plurality of bubble images on the outer edges of the near side display layer, and moves the band images 450 to the central portion as the user approaches the destination. These band images 450 can serve as an example of vehicle travelling information related to travelling of the vehicle. In this way, the user can understand more stereoscopically and dynamically that the user himself or herself is approaching the destination.

Notification that a Plurality of Users are Directed Towards a Same Destination)

Figure 31:
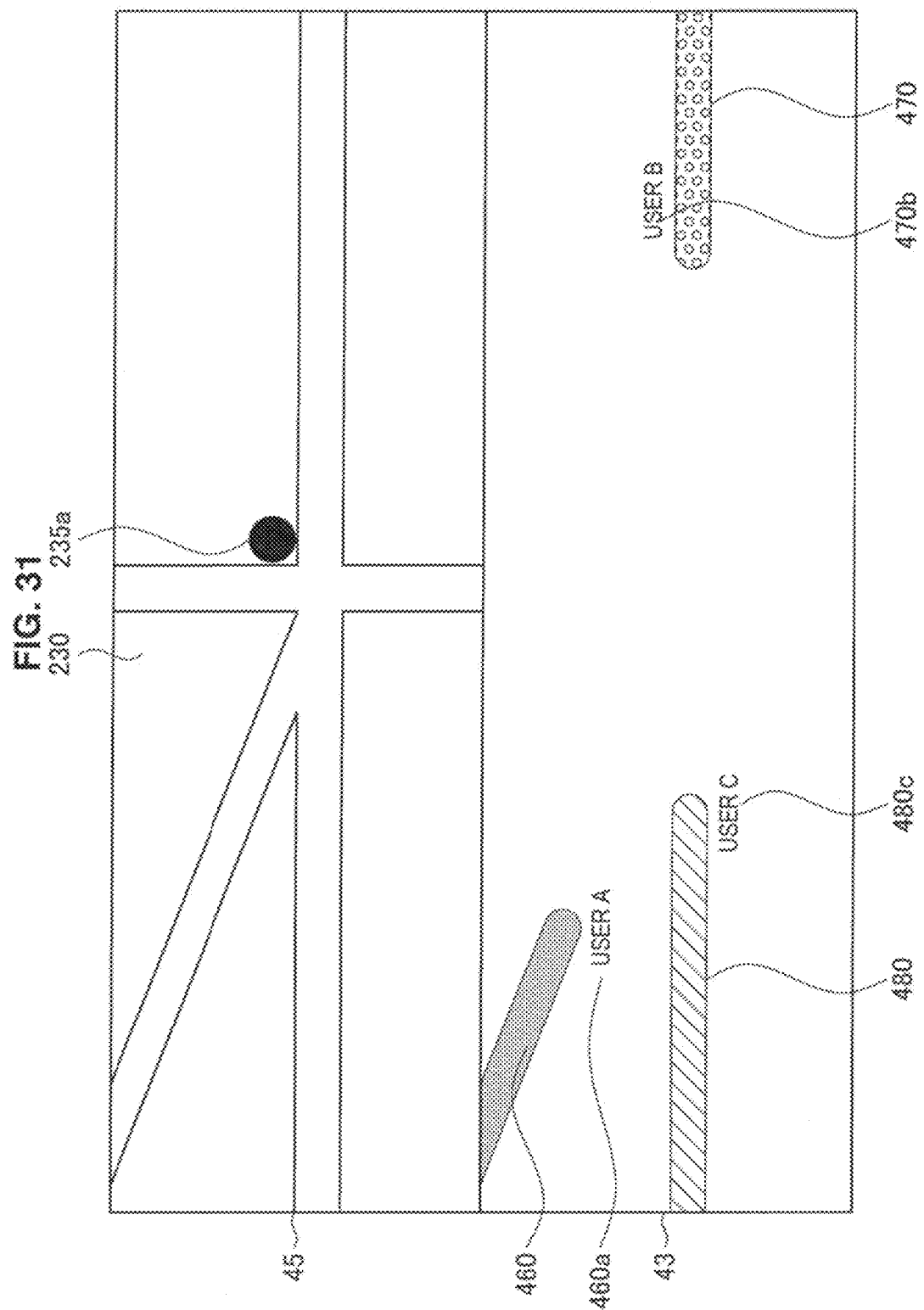
FIG. 31 is an explanatory diagram which shows an example of an image displayed on the display section.
Figure 32:
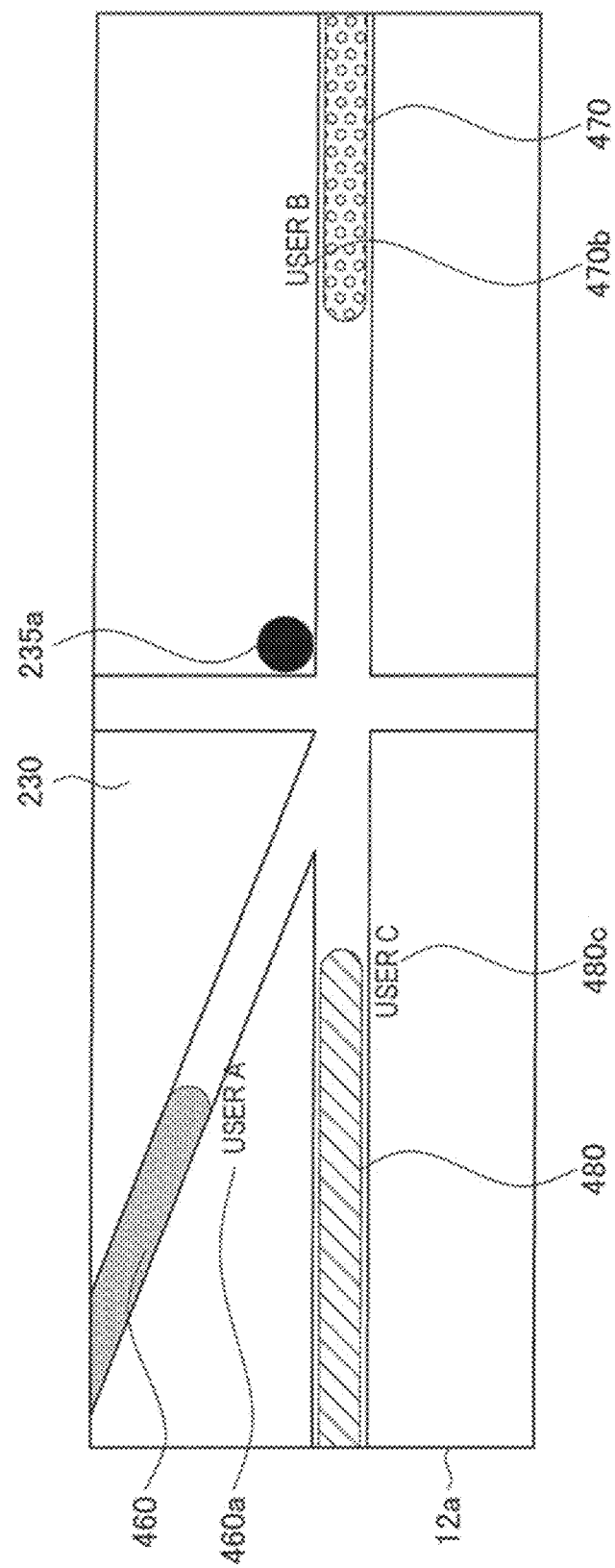
FIG. 32 is an explanatory diagram which shows an example of an image displayed on the front surface of the information processing apparatus.

Next, an example in which notification is performed that a plurality of users are directed towards a same destination will be described based on FIG. 31 to FIG. 32. FIG. 31 shows display target information displayed on the first display region 43 and the second display region 45 of the display section 40. FIG. 32 shows display target information displayed on the front surface 12a of the information processing apparatus 10. In this example, the communication section 101 receives present position information of other users, and outputs this received present position information to the display control section 104.

The display control section 104 displays map information 230 and a destination marker 235a on the interior side display layer. On the other hand, the display control section 104 displays band images 460 to 480 which show a movement locus of each of the users, and icons 460a to 480a which show each of the users, on the near side display layer. The leading edges of the band images 460 to 480 show the present positions of the other users. In the case where the other users are moving in vehicles, the band images 460 to 480 and the icons 460a to 480a can serve as an example of vehicle travelling information related to travelling of the vehicles. In this way, the user can obtain an actual sense that the user is directed towards the destination together with the other users. This example is effective when performed, for example, in the case where a plurality of users have determined to gather at a same destination in the example of FIG. 25. The band images 460 to 480 and the icons 460a to 480a may be displayed in mutually different states (luminance, color or the like).

Example of Visually Sensing a Fuel Charge)

Figure 33:
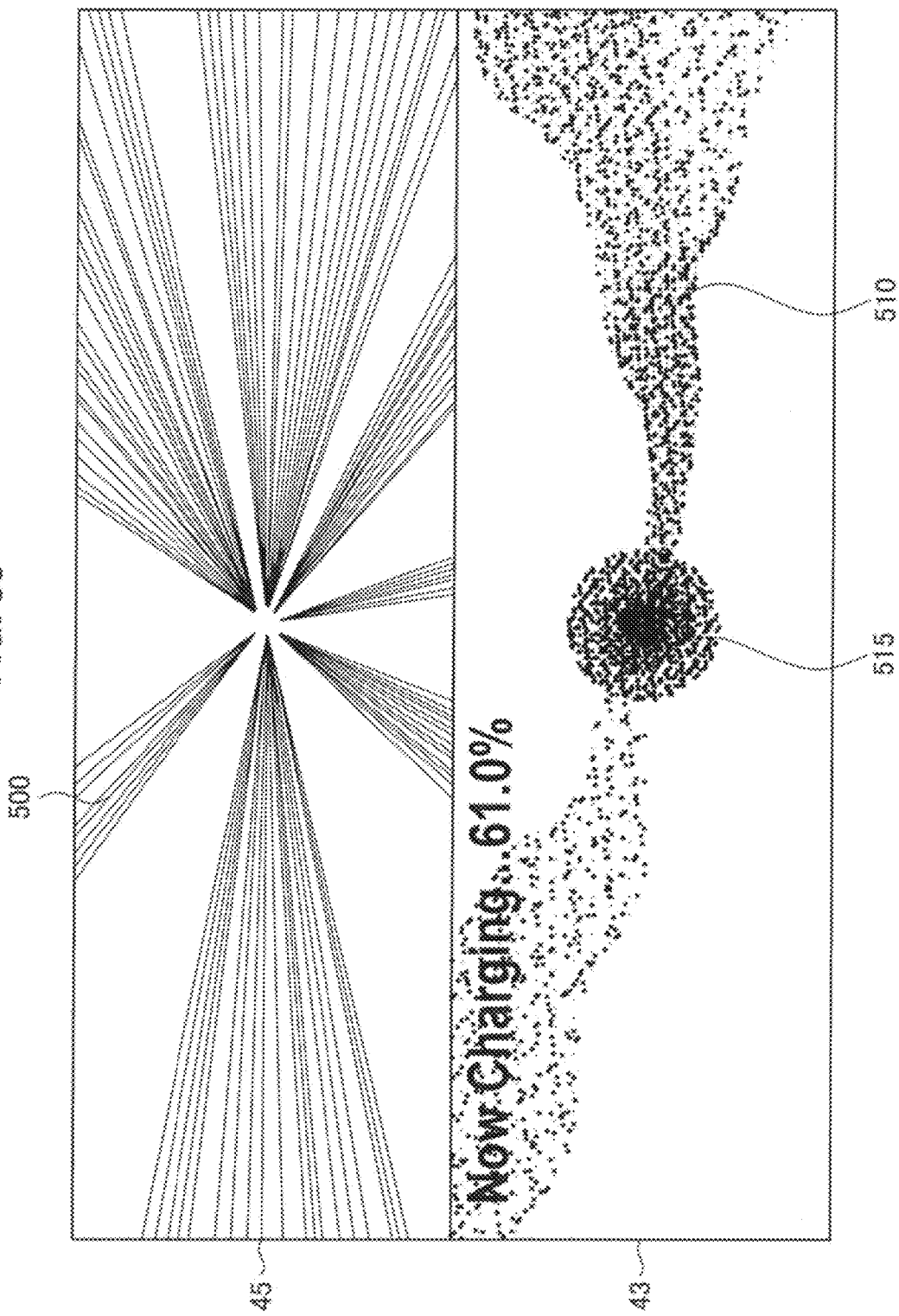
FIG. 33 is an explanatory diagram which shows an example of an image displayed on the display section.
Figure 34:
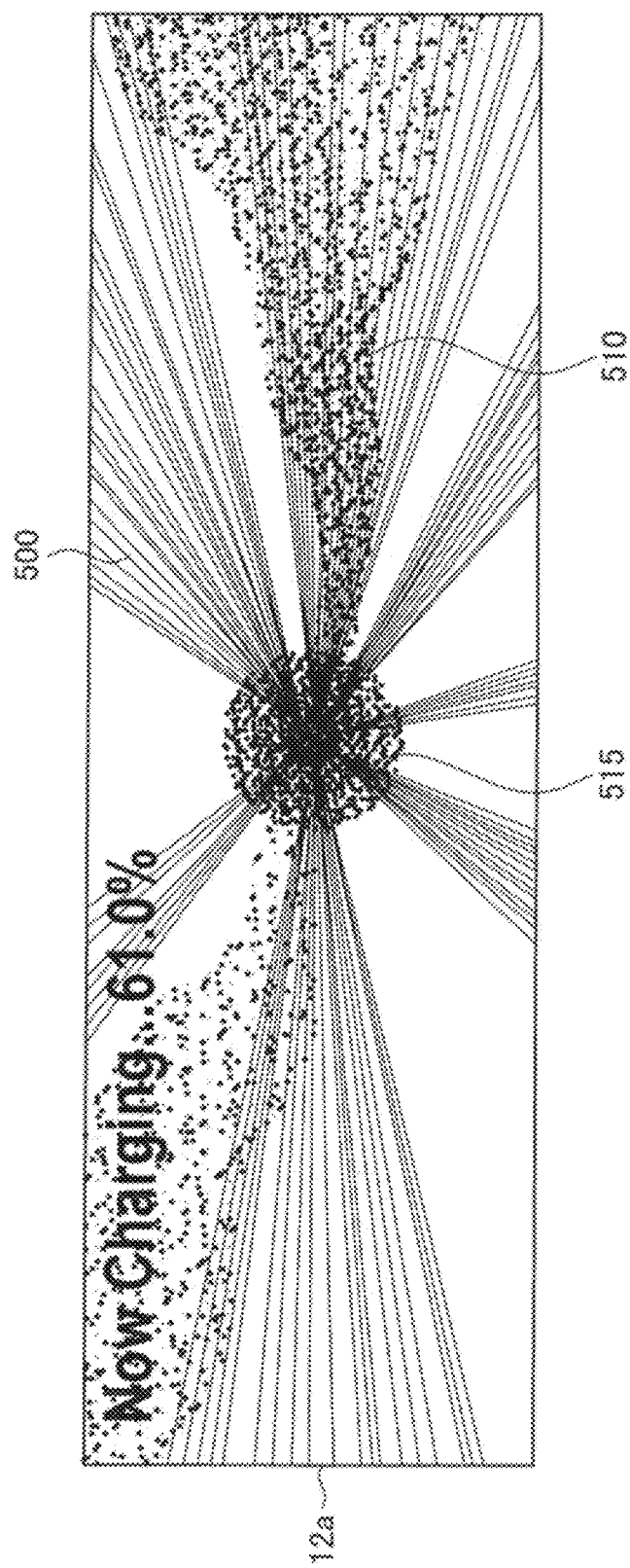
FIG. 34 is an explanatory diagram which shows an example of an image displayed on the front surface of the information processing apparatus.

Next, an example in which a fuel charge is visually sensed by the user will be described based on FIG. 33 and FIG. 34. FIG. 33 shows display target information displayed on the first display region 43 and the second display region 45 of the display section 40. FIG. 34 shows display target information displayed on the front surface 12a of the information processing apparatus 10.

As shown in FIG. 33, the display control section 104 displays line images 500, from the outer edges of the interior side display layer towards the central portion, on the interior side display layer. On the other hand, the display control section 104 displays band images 510 constituted from a plurality of bubble images, and character information which shows an accumulated value of fuel, on the near side display layer. The display control section 104 moves the band images 510 from the outer edges towards the central portion of the near side display layer, and terminates the band images. In this way, the flow of energy attracted to the central portion, that is, the fuel charged to the vehicle, can be visually sensed by the user. In other words, the display control section 104 can allow the user to intuitively and stereoscopically understand that fuel is being charged. This example deals with energy emotionally. The display control section 104 may display a globe 515 on the central portion of the near side display layer. In this way, the display control section 104 can realize a state in which energy is consolidated into the globe 515.

(Overlapping Display of a Panoramic Image and Object-Related Images Related to Objects)

Figure 35:
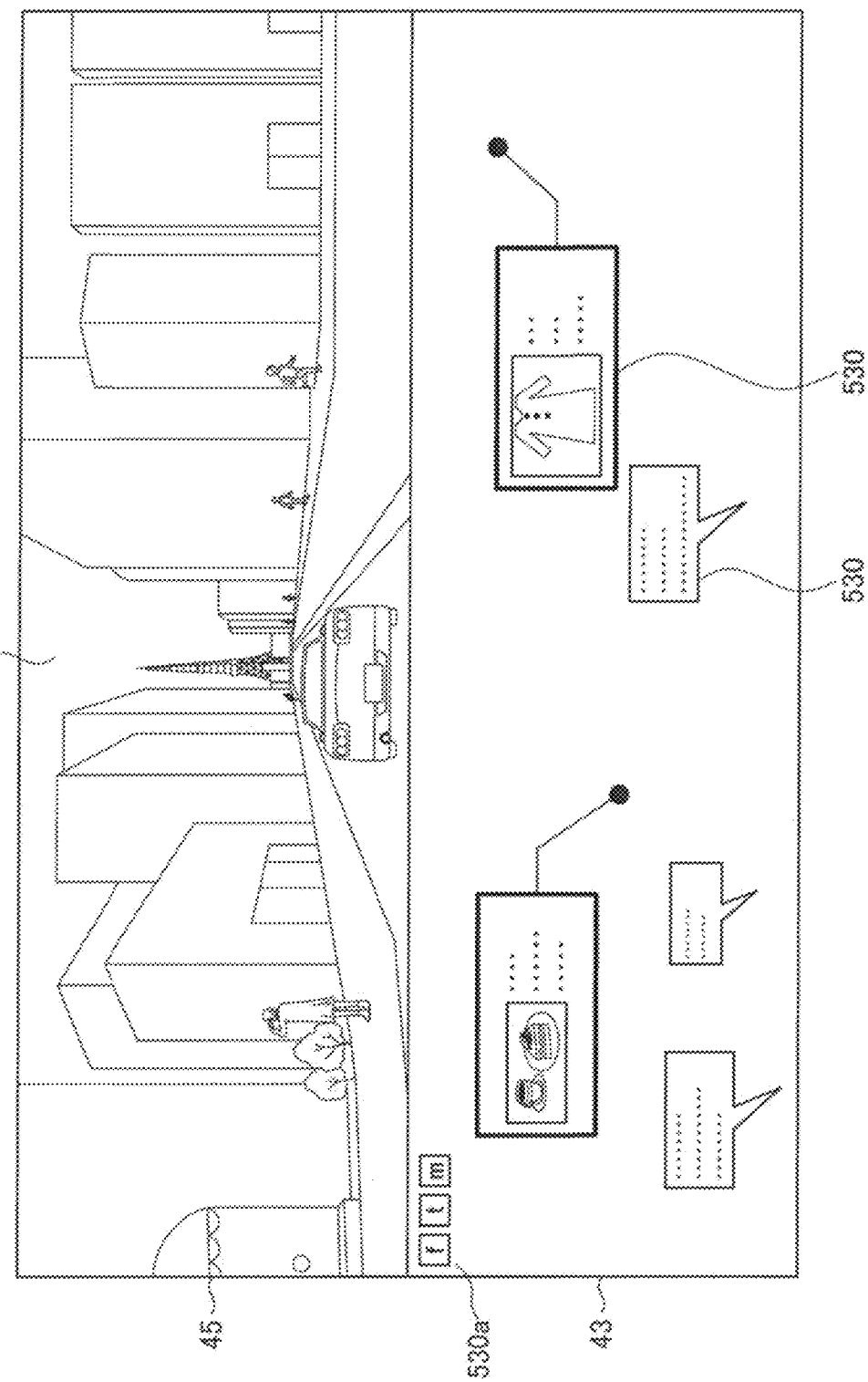
FIG. 35 is an explanatory diagram which shows an example of an image displayed on the display section.
Figure 36:
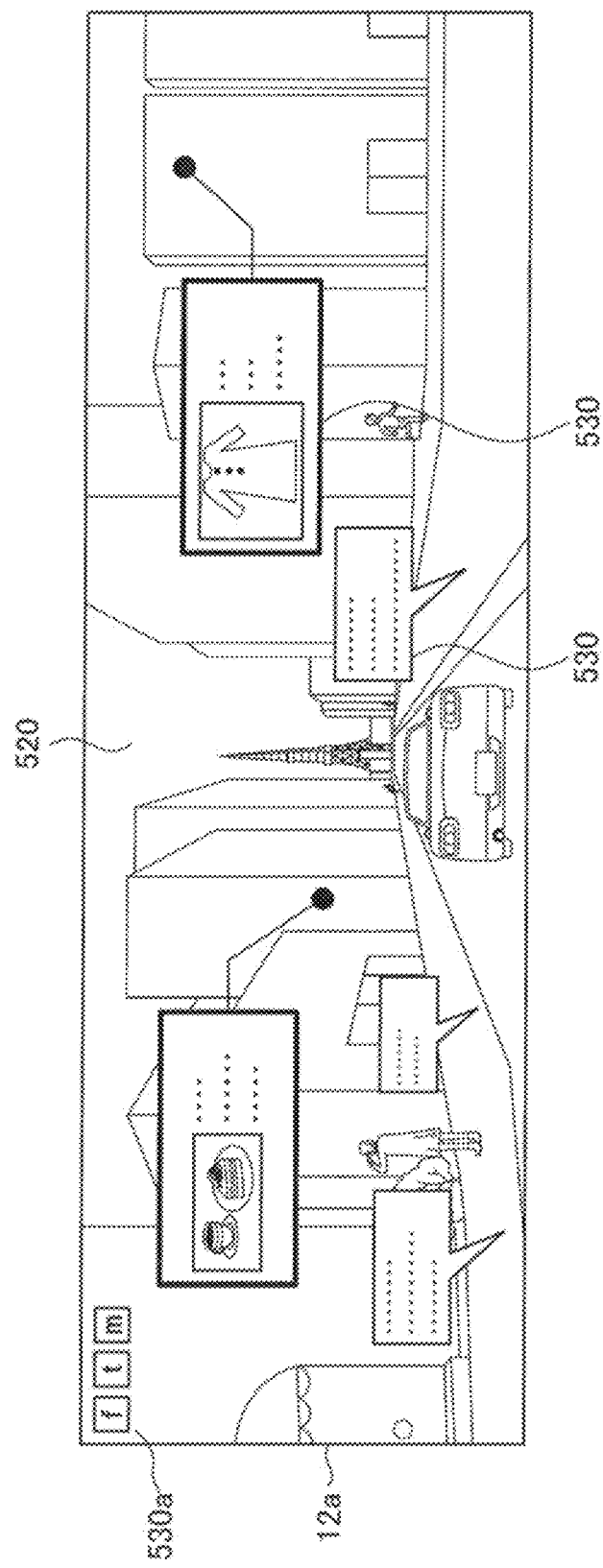
FIG. 36 is an explanatory diagram which shows an example of an image displayed on the front surface of the information processing apparatus.

Next, an example in which a panoramic image and object-related images related to objects are displayed overlapping will be described based on FIG. 35 and FIG. 36. FIG. 35 shows display target information displayed on the first display region 43 and the second display region 45 of the display section 40. FIG. 36 shows display target information displayed on the front surface 12a of the information processing apparatus 10. This example is similar to a so-called augmented reality (AR).

The display control section 104 displays a panoramic image 520 (for example, imaging the surroundings of the vehicle) on the interior side display layer, and displays object-related information 530 related to each object of the panoramic image 520 at positions overlapping the objects from within the near side display layer. The object-related information 530 is word-of-mouth communication contributed from each of the users related to these objects, advertising messages contributed from the owners of the objects or the like. Further, the display control section 104 may display icons 530a, which show links to different types of SNS, on the near side display layer so that users can contribute word-of-mouth communication or the like from this screen. Note that, the icons 530a may be displayed such as in the other examples.

(Stereoscopically Displaying Icons of Other Users)

Figure 37:
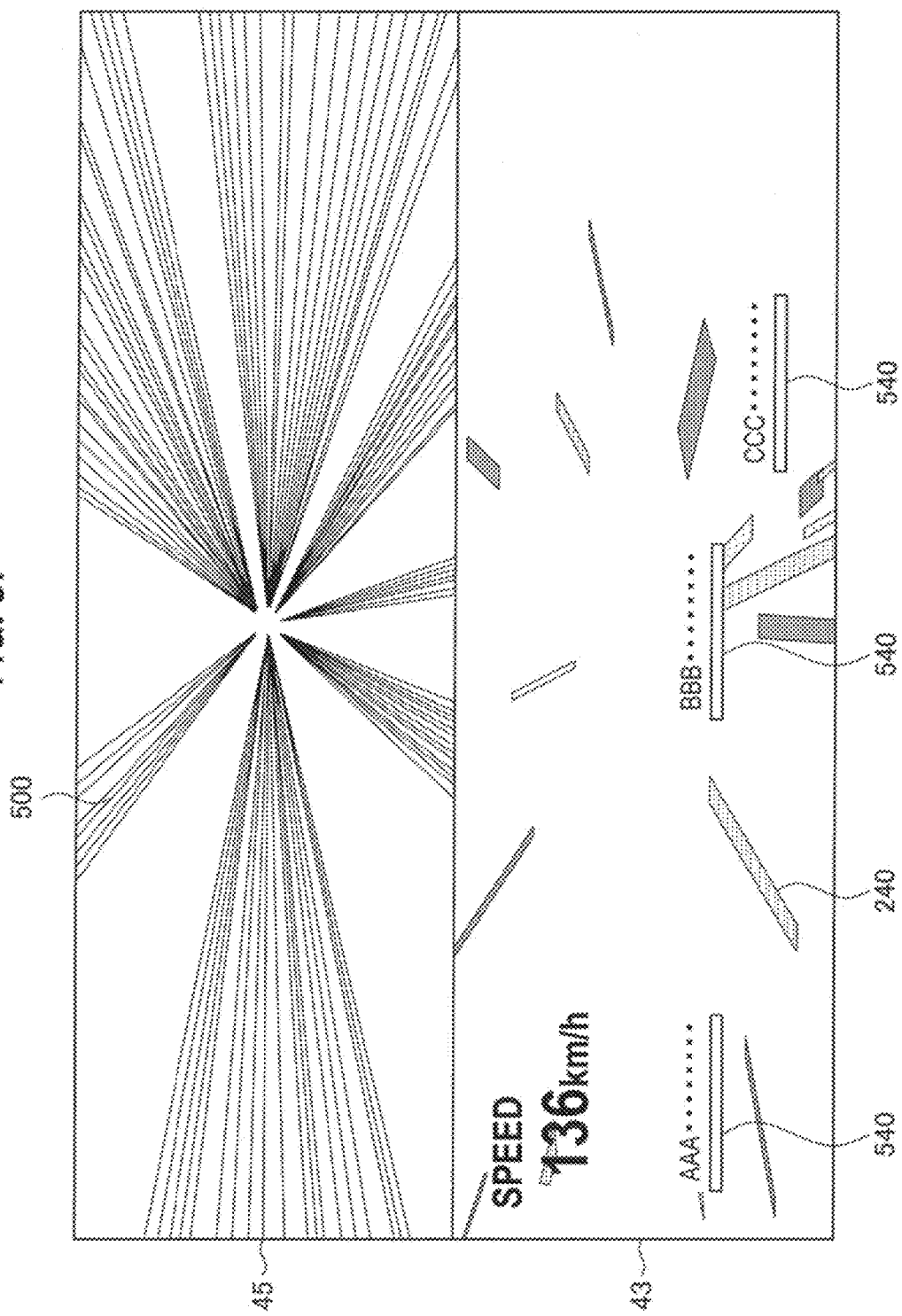
FIG. 37 is an explanatory diagram which shows an example of an image displayed on the display section.
Figure 38:
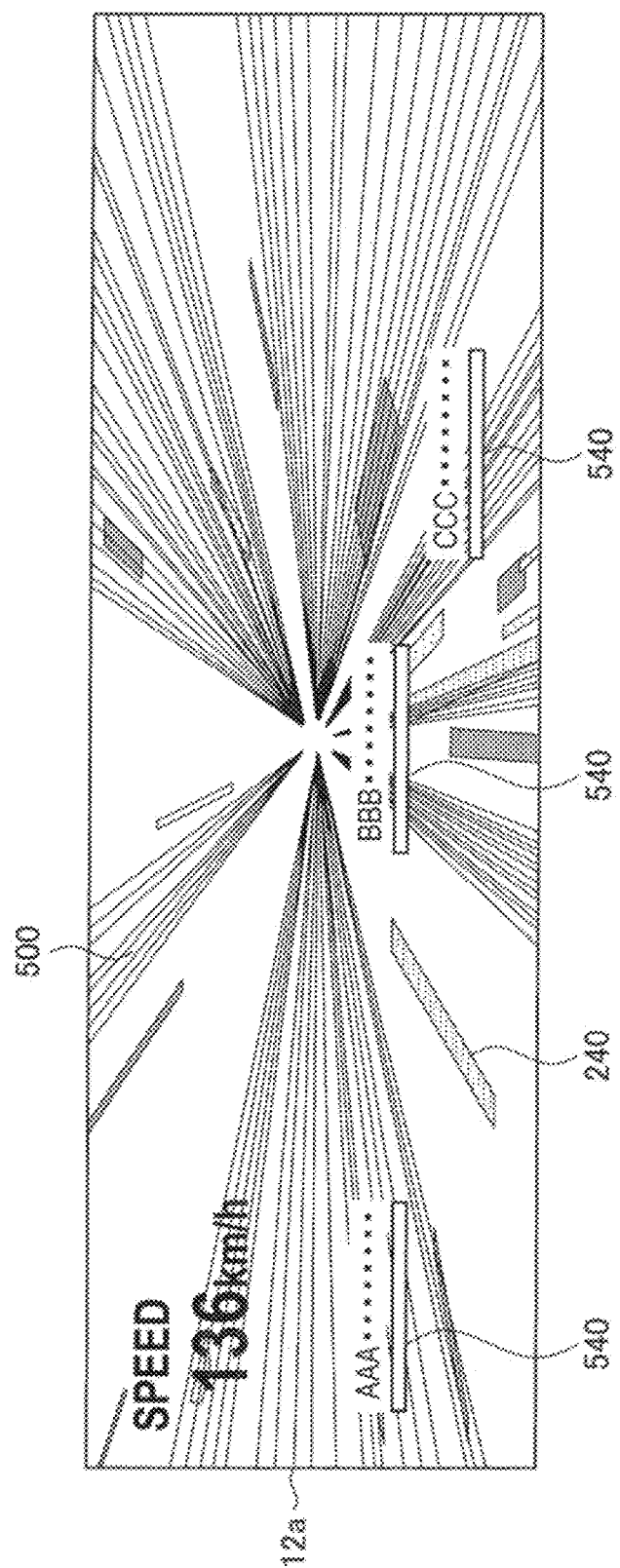
FIG. 38 is an explanatory diagram which shows an example of an image displayed on the front surface of the information processing apparatus.

Next, an example in which icons of other users are stereoscopically displayed will be described based on FIG. 37 and FIG. 38. FIG. 37 shows display target information displayed on the first display region 43 and the second display region 45 of the display section 40. FIG. 38 shows display target information displayed on the front surface 12a of the information processing apparatus 10. In this example, the communication section 101 receives present position information and destination information of other users, and outputs the received information to the display control section 104. Hereinafter, the user of the information processing apparatus 10 will be called a main user, and users other than the main user will be called other users.

As shown in FIG. 37, the display control section 104 displays an image the same as that of FIG. 33 on the interior side display layer. The display control section 104 displays icons 540 which represent other users (for example, number plate numbers which show vehicles the other users are driving, face photographs of the other users, photographs of the vehicles, user names or the like), and the above described rectangular images 240, on the near side display layer. The display control section 104 may display the vehicle speed information 200 on the near side display layer. In this way, the user can intuitively know that each of the icons 540 is moving within a three-dimensional space.

The display control section 104 displays the icons 540 which represent the other users at display positions corresponding to the present positions of the other users. Some specific examples will be considered. For example, in the case where each user is directed towards a same destination, the display control section 104 sets an axis connecting the present position of the main user and the destination as an x-axis, and sets a direction from the present position of the main user towards the destination as a positive direction of the x-axis. Further, the display control section 104 sets an axis orthogonal to the x-axis as a y-axis. Also, the display control section 104 calculates x-y coordinates of the present positions of the other users. In addition, the display control section 104 also sets an x-y axis within the near side display layer. That is, the display control section 104 assumes that the central portion of the near side display layer is the destination. Also, the display control section 104 sets an axis from the outer edges of the near side display layer towards the central portion as an x-axis (the depth direction is a positive direction), and sets an axis orthogonal to the x-axis as a y-axis. Also, the display control section 104 displays the icons 540 of each user at display positions corresponding to the x-y coordinates of each of the users. Therefore, the icons 540 of these users are displayed at positions nearer to the outer edges of the near side display layer as the distance from the destination up to each user increases. Further, in the case where the other users are present on the right side with respect to the progress direction of the main user, the icons 540 of these users are displayed on the right side from the central portion of the near side display layer. According to this example, the main user can intuitively judge how near the other users are approaching with respect to the destination. In this example, the main user can obtain a shared sense of time and actions with the other users. While the other users are assumed to have a friend relationship on a network with the main user, the relationship between users is not particularly taken into account.

Having respectively different destinations for each user, and assuming that the destination of each user is at the central portion of the near side display layer, can be included as another example. In this example, the display control section 104 sets an axis connecting the present position of the main user and the destination as a reference axis, and sets an axis orthogonal to the reference axis as a y-axis. Also, the display control section 104 sets axes connecting the present positions of the other users and the destinations of the other users as x-axes, and sets directions from the present positions of the other users towards the destinations of the other users as x-axis positive directions. That is, an x-axis is set for each user. In addition, the display control section 104 also sets an x-y axis within the near side display layer. That is, the display control section 104 assumes that the central portion of the near side display layer is the destination for each user. Also, the display control section 104 sets an axis from the outer edges of the near side display layer towards the central portion as an x-axis (the depth direction is a positive direction), and sets an axis orthogonal to the x-axis as a y-axis. Also, the display control section 104 displays the icons 540 of each user at display positions corresponding to the x-y coordinates of each of the users. Therefore, the icons 540 of these users are displayed at positions nearer to the outer edges of the near side display layer as the distance from the each user's destination up to each user increases. According to this example, the main user can intuitively judge how near the other users are approaching with respect to the destination, even in the case where the destination is different from that of the other users. In this example, the main user can obtain a shared sense of time and actions with the other users, even in the case where the other users act with different purposes to that of the main user, which are completely unrelated to the main user. It is needless to say that the other users may have a friend relationship on a network with the main user. That is, the relationship between users is not particularly taken into account.

In addition, indicating other users who are present between the present position of the main user and the destination can be included as another example. In this example, the display control section 104 sets an axis connecting the present position of the main user and the destination as an x-axis, and sets a direction from the present position of the main user towards the destination as a positive direction of the x-axis. Further, the display control section 104 sets an axis orthogonal to the x-axis as a y-axis. Also, the display control section 104 calculates x-y coordinates of the present positions of the other users. In addition, the display control section 104 also sets an x-y axis within the near side display layer. That is, the display control section 104 assumes that the central portion of the near side display layer is the destination. Also, the display control section 104 sets an axis from the outer edges of the near side display layer towards the central portion as an x-axis (the depth direction is a positive direction), and sets an axis orthogonal to the x-axis as a y-axis. Also, the display control section 104 displays the icons 540 of each user at display positions corresponding to the x-y coordinates of each of the users.

While this example is similar to the first example, it may not be necessary for each user to proceed towards the destination. That is, the users directed towards the destination may be only the main user, and the other users may remain at the present position, for example, to eat, sleep or the like. That is, the display control section 104 expresses what each user is doing in a form such as the movement of the icons 540. In this example, the main user can obtain a shared sense of time and actions with the other users, even in the case where the other users act with different purposes to that of the main user, which are completely unrelated to the main user. It is needless to say that the other users may have a friend relationship on a network with the main user. That is, the relationship between users is not particularly taken into account.

In each of the above described examples, the icons 540 of each user may be normally displayed, or may be displayed, for example, at a timing at which each user transmits (contributes) messages (tweets) to the main user. Further, the display control section 104 may display only the direction of movement of the other users on the near side display layer or the interior side display layer. Further, the display control section 104 may display the icons 540 of users close to the destination near the central portion of the interior side display layer, and may display the icons 540 of users far from the destination near the outer edges of the near side display layer. That is, the display control section 104 may divide the display layer of the icons 540 in accordance with the distances from the present positions of the other users up to the destination.

(Display of a Game Screen)

Figure 39:
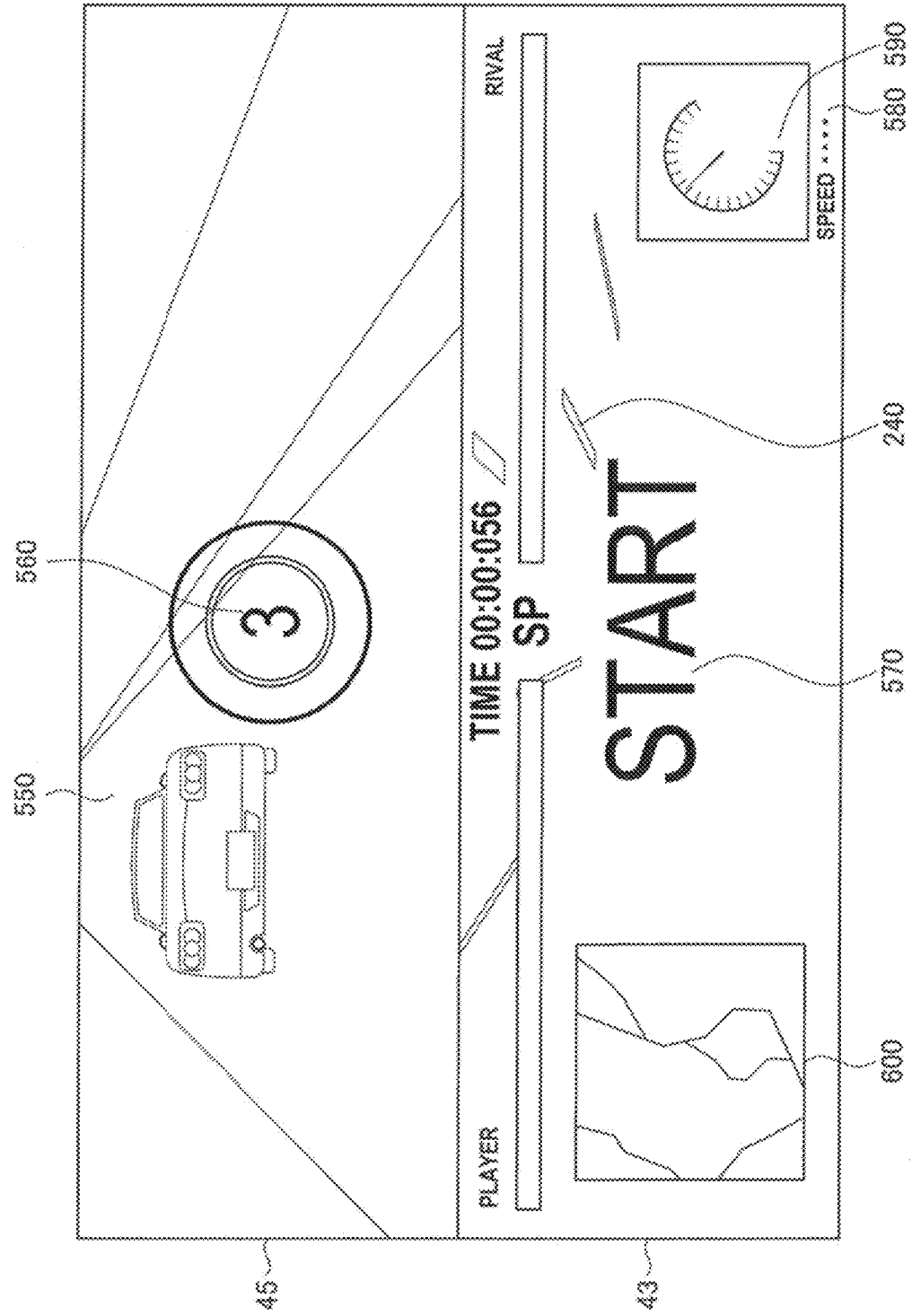
FIG. 39 is an explanatory diagram which shows an example of an image displayed on the display section.
Figure 40:
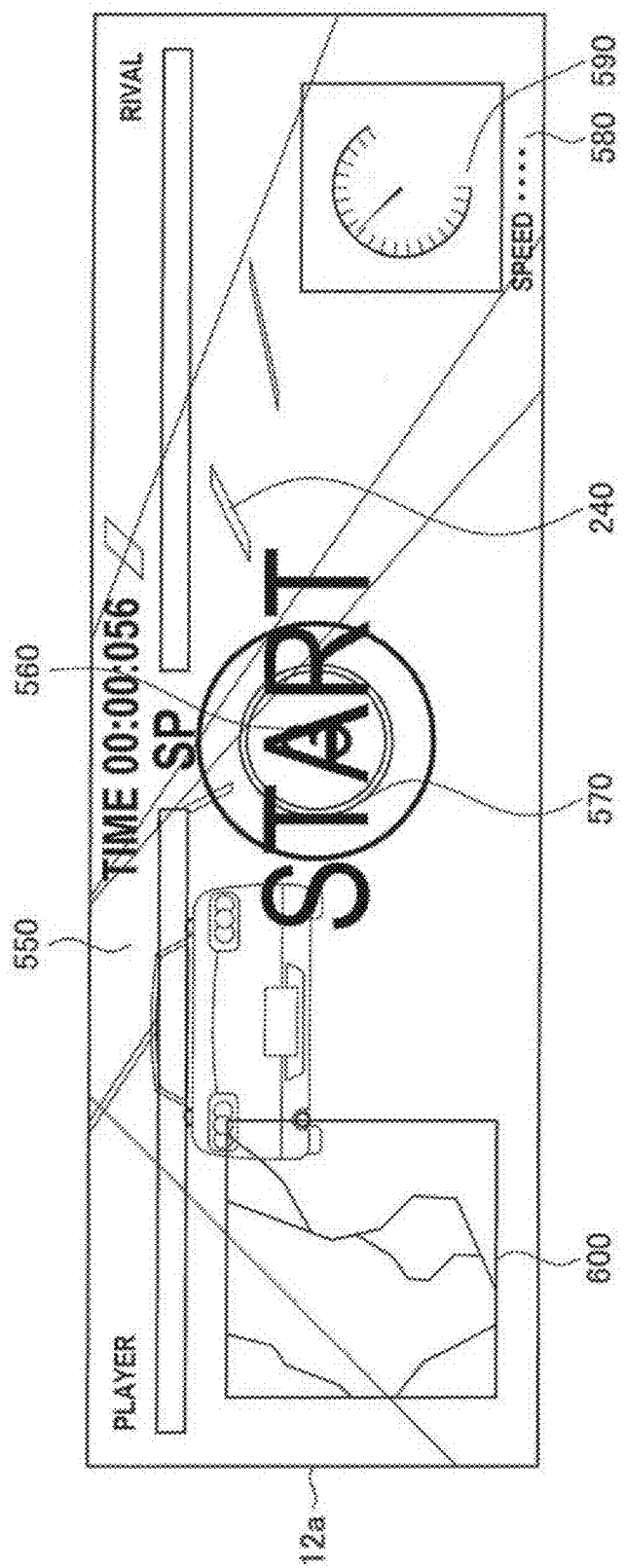
FIG. 40 is an explanatory diagram which shows an example of an image displayed on the front surface of the information processing apparatus.

An example in which a racing game screen is stereoscopically displayed will be described based on FIG. 39 to FIG. 40. FIG. 39 shows display target information displayed on the first display region 43 and the second display region 45 of the display section 40. FIG. 40 shows display target information displayed on the front surface 12a of the information processing apparatus 10.

In this example, the display control section 104 displays a course image 550, a count image 560 which shows the remaining count number up to the game start or the like, from among images constituting a racing game screen, on the interior side display layer. The display control section 104 displays a character image 570 which signals the game start, various user interfaces (a speed meter 580, a tachometer 590 and map information 600) or the like on the near side display layer. The display control section 104 may display the above described rectangular images 240 on the near side display layer. In this way, the user can more stereoscopically recognize the racing game screen. Note that, the types of images displayed on the near side display layer and the interior side display layer are not limited to those described above. Note that, the character image 570 may be enlarged each time the count number of the count image 560 becomes small. According to this example, the user can enjoy a game which provides a more realistic feeling. Note that, the game capable of being displayed by the information processing apparatus 10 is not limited to a racing game.

(Displaying an Image with a Size Corresponding to a Viewpoint Position of the User)

Figure 41:
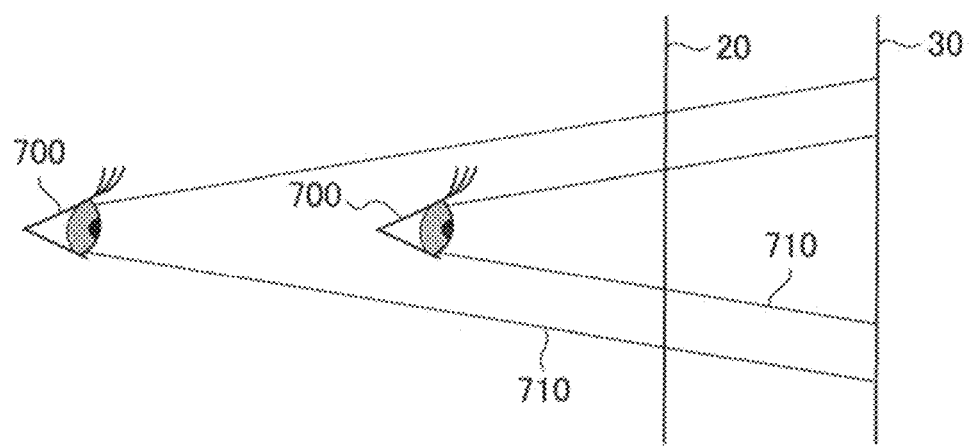
FIG. 41 is a side surface view which shows a correspondence relation between a distance from a viewpoint of a user up to each of the display layers, and a visual field of the user.

Next, an example in which an image is displayed with a size corresponding to a viewpoint position of the user will be described based on FIG. 41. FIG. 41 shows a relation between a distance from each of the display layers (half mirror 20 and mirror 30) up to a viewpoint 700 of the user, and the visual field 710 of the user. Note that, in order to facilitate understanding in FIG. 41, each of the display layers extends in a vertical direction (as shown in FIG. 1B, each of the display layers are actually inclined with respect to a vertical direction).

As shown in FIG. 41, an intersecting region (a region which can be visually recognized by the user) between the visual field 710 of the user and each of the display layers decreases as the distance from the viewpoint 700 of the user up to each of the display layers decreases. Accordingly, the display control section 104 reduces the image to be displayed on each of the display layers as the distance from the viewpoint 700 of the user up to each of the display layers decreases. Note that, for example, it is possible for the distance from the viewpoint 700 of the user up to each of the display layers to be distinguished by information from the motion sensor 103. In this way, the user can more accurately and visually recognize information displayed on each of the display layers.

According to the present embodiment as described above, the display control section 104 determines information to be displayed on each of a plurality of mutually overlapping display layers, based on parameters associated with this information. Therefore, since the information processing apparatus 10 can more appropriately determine information to be displayed on each of the display layers, each of the display layers can be more effectively used.

In addition, since the display control section 104 determines information to be displayed on each of the plurality of display layers, based on a magnitude relation of the parameters, information to be displayed on each of the display layers can be more appropriately determined.

In addition, since the display control section 104 determines information to be displayed on each of the plurality of display layers, based on the parameters and a threshold corresponding to the parameters, information to be displayed on each of the display layers can be more appropriately determined.

In addition, since it is possible for the display control section 104 to move information displayed on any one of the display layers to another display layer, each type of information can be more dynamically displayed.

In addition, the display control section 104 displays information on one of the display layers, then also displays the information displayed on the one of the display layers on another display layer, and then reduces the visibility of the information displayed on the one of the display layers. Therefore, the display control section 104 can more continuously (naturally) perform movement of information between display layers.

In addition, since the display control section 104 reduces the visibility of the information displayed on the one of the display layers, by reducing the luminance of the information displayed on the one of the display layers (performs a so-called luminance exchange), the display control section 104 can more continuously (naturally) perform movement of information between display layers.

The display control section 104 moves (for example, enlarges) the size of the information displayed on the one of the display layers. Next, the display control section 104 also displays the information displayed on the one of the display layers on another display layer, and then moves (for example, enlarges both) the information displayed on the one of the display layers and the information displayed on the another display layer in a same state. Therefore, the display control section 104 can more continuously (naturally) perform movement of information between display layers.

In addition, since the display control section 104 adjusts parameters based on operations of the user, the display control section 104 can more appropriately determine information to be displayed on each of the display layers.

In addition, the display control section 104 determines information to be displayed on each of the display layers based on priorities. Specifically, the display control section 104 displays information estimated to be necessary for the user on the near side display layer, and displays other information on the interior side display layer. Therefore, the display control section 104 can more appropriately determine information to be displayed on each of the display layers.

In addition, since the display control section 104 displays vehicle travelling information and map information on separate display layers, the user can intuitively and stereoscopically understand this information.

In addition, since the display control section 104 displays vehicle travelling information related to travelling of the vehicle and vital information of the driver on separate display layers, the user can intuitively and stereoscopically understand this information.

In addition, the display control section 104 displays captured images corresponding to a requirement of the user, from among captured images obtained by imaging each direction of the surroundings of the vehicle, on the near side display layer, and displays other captured images on the interior side display layer. Therefore, the user can intuitively and stereoscopically understand this information.

In addition, the display control section 104 displays captured images obtained by imaging each direction of the surroundings of the vehicle on the interior side display layer, and displays indication images, which show objects to be visually recognized by the user from among the captured images, on the near side display layer. Therefore, the user can intuitively and stereoscopically understand this information.

In addition, the display control section 104 displays captured images obtained by imaging each direction of the surroundings of the vehicle on the interior side display layer, and displays object-related information related to objects within the captured images on the near side display layer. Therefore, the user can intuitively and stereoscopically understand this information.

In addition, the display control section 104 displays captured images corresponding to a requirement of the user, from among the captured images captured at a position where the vehicle is estimated to arrive, on the near side display layer, and displays other captured images on the interior side display layer. Therefore, the user can intuitively and stereoscopically understand this information.

In addition, the display control section 104 displays messages from other users on the near side display layer, and displays information related to the users who have transmitted the messages on the interior side display layer. Therefore, the user can intuitively and stereoscopically understand this information.

In addition, the display control section 104 displays icons which represent other users at display positions corresponding to the present positions of the other users within the near side display layer, and displays line images, on the interior side display layer, which extend from the outer edges of the interior side display layer to the central portion. Therefore, the user can intuitively and stereoscopically understand this information.

In addition, since the display control section 104 determines a size of information to be displayed on each of the display layers based on the distance from the viewpoint of the user up to each of the display layers, the user can more accurately and visually recognize information displayed on each of the display layers.

It should be understood by those skilled in the art that various modifications, combinations, sub-combinations and alterations may occur depending on design requirements and other factors insofar as they are within the scope of the appended claims or the equivalents thereof.

For example, while the plurality of display layers are implemented in the above described embodiment by using a half mirror 20 and a mirror 30, the plurality of display layers may be implemented by stacking displays having transparency. That is, an implementation method of multiple display layers is not taken into account. Additionally, the present technology may also be configured as below.

(1) An information processing apparatus, including a display control section which determines information to be displayed on each of a plurality of mutually overlapping display layers based on parameters associated with this information.

(2) The information processing apparatus according to (1),
wherein the display control section determines information to be displayed on each of the plurality of display layers based on a magnitude relation of the parameters.

(3) The information processing apparatus according to (1) or (2),
wherein the display control section determines information to be displayed on each of the plurality of display layers based on the parameters and a threshold corresponding to the parameters.

(4) The information processing apparatus according to any one of (1) to (3),
wherein the display control section is capable of moving information displayed on any one of the display layers to another display layer.

(5) The information processing apparatus according to (4),
wherein the display control section displays information on one of the display layers, then also displays the information displayed on the one of the display layers on the another display layer, and then reduces visibility of the information displayed on the one of the display layers.

(6) The information processing apparatus according to (5),
wherein the display control section reduces visibility of the information displayed on the one of the display layers by reducing luminance of the information displayed on the one of the display layers.

(7) The information processing apparatus according to (5),
wherein the display control section changes a size of the information displayed on the one of the display layers, then also displays the information displayed on the one of the display layers on the another display layer, and then changes a size of the information displayed on the one of the display layers and a size of the information displayed on the another display layer in a same state.

(8) The information processing apparatus according to any one of (1) to (7),
wherein the display control section adjusts the parameters based on operations of a user.

(9) The information processing apparatus according to any one of (1) to (8),
wherein the display control section displays information estimated to be necessary for a user on any one of the display layers, and displays other information on another display layer arranged at a position farther from a viewpoint of the user than a position of the one of the display layers.

(10) The information processing apparatus according to any one of (1) to (9),
wherein the display control section displays vehicle travelling information related to travelling of a vehicle, and map information, on separate display layers.

(11) The information processing apparatus according to any one of (1) to (10),
wherein the display control section displays vehicle travelling information related to travelling of a vehicle, and vital information of a driver, on separate display layers.

(12) The information processing apparatus according to any one of (1) to (11),
wherein the display control section displays captured images corresponding to a requirement of a user, from among captured images obtained by imaging each direction of surroundings of a vehicle, on any one of the display layers, and displays other captured images on another display layer.

(13) The information processing apparatus according to any one of (1) to (12),
wherein the display control section displays captured images obtained by imaging each direction of surroundings of a vehicle on one of the display layers, and displays indication images which show objects to be visually recognized by a user from among the captured images on another display layer.

(14) The information processing apparatus according to any one of (1) to (13),
wherein the display control section displays captured images obtained by imaging each direction of surroundings of a vehicle on one of the display layers, and displays object-related information related to objects within the captured images on another display layer.

(15) The information processing apparatus according to any one of (1) to (14),
wherein the display control section displays captured images corresponding to a requirement of a user, from among captured images captured at a position where a vehicle is estimated to arrive, on any one of the display layers, and displays other captured images on another display layer.

(16) The information processing apparatus according to any one of (1) to (15),
wherein the display control section receives messages from a communication section capable of receiving messages, displays the messages on any one of the display layers, and displays information related to users who have transmitted the messages on another display layer.

(17) The information processing apparatus according to any one of (1) to (16),
wherein the display control section displays an icon which represents another user at a display position corresponding to a present position of the another user within any one of the display layers, and displays a line image on another display layer, the line image extending from outer edges of the another display layer to a reference point set within the another display layer.

(18) The information processing apparatus according to any one of (1) to (17),
wherein the display control section determines a size of information to be displayed on each of the display layers based on a distance from a viewpoint of a user up to each of the display layers.

(19) An information processing method, including determining information to be displayed on each of a plurality of mutually overlapping display layers based on parameters associated with this information.

(20) A program for causing a computer to function as a display control function which determines information to be displayed on each of a plurality of mutually overlapping display layers based on parameters associated with this information.

What is claimed is:

1. An information processing apparatus comprising: circuitry configured to:
  control display of a front viewing surface of a display device, the display device having an interior display and a near display;
  wherein the interior display and the near display provide an overlapping visual of a first image and a second image, onto the front viewing surface of the display device, wherein the interior display has a depth that is further from the front viewing surface than a depth of the near display thereby creating a depth perception of the overlapping visual;
  wherein the first image includes information sourced from an image capture device of a vehicle, the first image is an image captured of what is located in front of the vehicle second image is different from the first image, the second image is associated with the first image and is an indication image bringing attention to content of the first image;
  associate a priority to the first image;
  associate a priority to the second image;
  based upon the associated first image priority, assign the near display to present the first image;
  based upon the associated second image priority, assign the interior display to present the second image;
  detect an operation of the user;
  based upon the detected operation of the user, switch the priorities so the interior display is assigned to the first image and the near display is assigned to the second image, to create a change in the depth perception of the overlapping visual.

2. The information processing apparatus according to claim 1, wherein a third image is obtained by imaging another direction of the surrounding of the vehicle, the other direction being different from the first direction.

3. The information processing apparatus according to claim 2, wherein the directions include a forward and a right side of the vehicle;
  and the circuitry is further configured to present the third image onto the front viewing surface simultaneously with the first image, but in a different location than a location of the first image.

4. The information processing apparatus according to claim 1, wherein the second image includes a frame of a person identified in the first image.

5. The information processing apparatus according to claim 4, wherein the second image includes a night vision viewability.

6. The information processing apparatus according to claim 3, wherein a fourth image is obtained by imaging a different direction of the surrounding of the vehicle; and
  the circuitry is further configured to present the fourth image onto the front viewing surface simultaneously with the first image and the third image, but in a different location than a location of the first image and the third image.

7. The information processing apparatus according to claim 1, wherein the circuitry is further configured to control display of the indication image so that the indication image is emphasized over the image of the front of the vehicle as an alert notice with the term ATTENTION.

8. The information processing apparatus according to claim 1, wherein the circuitry is further configured to control display of the indication image so that the indication image is emphasized over the image of the front of the vehicle.

9. The information processing apparatus according to claim 1, wherein the operation of the user is a change in line of sight.

10. The information processing apparatus according to claim 1, wherein the operation of the user is a movement of the head.

11. The information processing apparatus according to claim 1, wherein the operation of the user is a movement of the hands.

12. The information processing apparatus according to claim 1, wherein the the near display is a half mirror.

13. The information processing apparatus according to claim 1, wherein the the interior display mirror.

14. The information processing apparatus according to claim 1, wherein the display device includes a display screen section.

15. The information processing apparatus according to claim 14, wherein the display screen section is one of a CRT display device, a liquid crystal display device, a plasma display device, an EL display device or a lamp.

16. The information processing apparatus according to claim 1, wherein the circuitry is further configured to control display of the image based on overlapping information indicating that the vehicle is traveling.

17. The information processing apparatus according to claim 1, wherein the user is a driver of the vehicle.

18. A method comprising:
  controlling display of a front viewing surface of a display device, the display device having an interior display and a near display;
  wherein the interior display and the near display provide an overlapping visual of a first image and a second image, onto the front viewing surface of the display device, wherein the interior display has a depth that is further from the front viewing surface than a depth of the near display thereby creating a depth perception of the overlapping visual;
  wherein the first image includes information sourced from an image capture device of a vehicle, the first image is an image captured of what is located in front of the vehicle second image is different from the first image, the second image is associated with the first image and is an indication image bringing attention to content of the first image;
  associating a priority to the first image;
  associating a priority to the second image;
  based upon the associated first image priority, assigning the near display to present the first image;
  based upon the associated second image priority, assigning the interior display to present the second image;
  detecting an operation of the user;
  based upon the detected operation of the user, switching the priorities so the interior display is assigned to the first image and the near display is assigned to the second image, to create a change in the depth perception of the overlapping visual.

19. A non-transitory computer-readable medium encoded with computer readable instructions that, when executed by processing circuitry, cause the processing circuitry to perform a method comprising:
  controlling display of a front viewing surface of a display device, the display device having an interior display and a near display;
  wherein the interior display and the near display provide an overlapping visual of a first image and a second image, onto the front viewing surface of the display device, wherein the interior display has a depth that is further from the front viewing surface than a depth of the near display thereby creating a depth perception of the overlapping visual;

wherein the first image includes information sourced from an image capture device of a vehicle, the first image is an image captured of what is located in front of the vehicle second image is different from the first image, the second image is associated with the first image and is an indication image bringing attention to content of the first image;

associating a priority to the first image;

associating a priority to the second image;

based upon the associated first image priority, assigning the near display to present the first image;

based upon the associated second image priority, assigning the interior display to present the second image;

detecting an operation of the user;

based upon the detected operation of the user, switching the priorities so the interior display is assigned to the first image and the near display is assigned to the second image, to create a change in the depth perception of the overlapping visual.

* * * * *